US010328127B2

(12) United States Patent
Chopra et al.

(10) Patent No.: US 10,328,127 B2
(45) Date of Patent: Jun. 25, 2019

(54) METHODS FOR STIMULATION OF APPETITE AND INCREASE IN WEIGHT BY ADMINISTRATION OF ASPROSIN

(71) Applicant: Baylor College of Medicine, Houston, TX (US)

(72) Inventors: Atul Chopra, Houston, TX (US); David D. Moore, Bellaire, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 15/038,435

(22) PCT Filed: Nov. 24, 2014

(86) PCT No.: PCT/US2014/067162
§ 371 (c)(1),
(2) Date: May 20, 2016

(87) PCT Pub. No.: WO2015/084625
PCT Pub. Date: Jun. 11, 2015

(65) Prior Publication Data
US 2016/0289289 A1    Oct. 6, 2016

Related U.S. Application Data

(60) Provisional application No. 62/073,501, filed on Oct. 31, 2014, provisional application No. 62/037,779, filed on Aug. 15, 2014, provisional application No. 62/010,557, filed on Jun. 11, 2014, provisional application No. 61/910,498, filed on Dec. 2, 2013.

(51) Int. Cl.
| | |
|---|---|
| *A61K 38/17* | (2006.01) |
| *A61K 38/22* | (2006.01) |
| *C07K 14/78* | (2006.01) |
| *C07K 14/575* | (2006.01) |
| *C07K 16/26* | (2006.01) |

(52) U.S. Cl.
CPC ............ *A61K 38/22* (2013.01); *C07K 14/575* (2013.01); *C07K 14/78* (2013.01); *C07K 16/26* (2013.01); *C07K 2317/76* (2013.01)

(58) Field of Classification Search
None
See application file for complete search history.

(56) References Cited

U.S. PATENT DOCUMENTS 6,497,875 B1    12/2002    Sorrell et al.

FOREIGN PATENT DOCUMENTS

WO    2003087768 A2    10/2003

OTHER PUBLICATIONS

Chaudhry et al. J. Cell Biol. 176(3): 355-367, 2007.*
Davis et al. Mol. Genet. Metab. 119)1-2_: 174-185, 2016.*
Ritty et al., "Processing of the fibrillin-1 carboxyl-terminal domain", J Biol Chem., Mar. 26, 1999, vol. 274, No. 13, pp. 8933-8940.
Hubmacher et al., "Biogenesis of extracellular microfibrils: Multimerization of the fibrillin-1 C terminus into bead-like structures enables self-assembly", Proc Natl Acad Sci USA, May 6, 2008, vol. 105, No. 18, pp. 6548-6553.
Database UniProt, Jun. 1, 2001 (Jun. 1, 2001), "SubName: Full= Fbn1 protein {EC0:0000313:EMBL:AAH03905.1}; Flags: Fragment;", XP002767700, retrieved from EBI accession No. UN I Prot: Q99 L19 Database accession.
Gaikwad et al., "Epigenetic changes and alteration of Fbn1 and Col3A1 gene expression under hyperglycaemic and hyperinsulinaemic conditions", Biochemical Journal, vol. 432, No. 2, Dec. 1, 2010, pp. 333-341.
Horn et al., "Progeroid facial features and lipodystrophy associated with a novel splice site mutation in the final intron of the FBN1 gene.", American Journal of Medical Genetics, Part A Apr. 2011, vol. 155A, No. 4, Apr. 2011, pp. 721-724.
Hartner et al, "Role of fibrillin-1 in hypertensive and diabetic glomerular disease.", American Journal of Physiology, Renal Physiology, Jun. 2006, vol. 290, No. 6, pp. F1329-F1336.
Lonnqvist et al., "Evidence for furin-type activity-mediated C-terminal processing of profibrillin-1 and interference in the processing by certain mutations", Human Molecular Genetics. vol. 7, No. 13, Dec. 1, 1998, pp. 2039-2044.
Nicoloff et al., "Serum fibrillin-antifibrillin immune complexes among diabetic children", Vascular Pharmacology, vol. 43, No. 3, Sep. 1, 2005, pp. 171-175, Elsevier, Amsterdam, NL.
Romere et al., "Asprosin, a Fasting-Induced Glucogenic Protein Hormone", Cell, vol. 165, No. 3, Apr. 14, 2016, pp. 566-579. Cell Press, US.
Sabin et al., "Genetics of obesity and overgrowth syndromes", Bailliere's Best Practice and Research, Clinical Endocrinologyand Metabolism, (2011) vol. 25, No. 1, pp. 207-220.
Takenouchi et al., "Severe congenital lipodystrophy and a progeroid appearance: Mutation in the penultimate exon of FBN1 causing recognizable phenotype.", American Journal of Medical Genetics, Part A Dec. 2013, vol. 161A, No. 12, Aug. 16, 2013, pp. 3057-3062.

*  cited by examiner (Continued)

*Primary Examiner* — Christine J Saoud
(74) *Attorney, Agent, or Firm* — Norton Rose Fulbright US LLP

(57) ABSTRACT

Embodiments of the disclosure concern methods and compositions that relate to increasing or decreasing the weight (including, for example, by increasing or decreasing the adipose mass) in individuals in need thereof. Such methods and compositions, in particular embodiments, concern providing an effective amount of the hormone asprosin to increase adipose mass in an individual with insufficient adipose mass and providing an antibody or inhibitor of asprosin in an individual with obesity or diabetes, for example, to reduce adipose mass.

6 Claims, 16 Drawing Sheets

Specification includes a Sequence Listing.

FIG. 1A

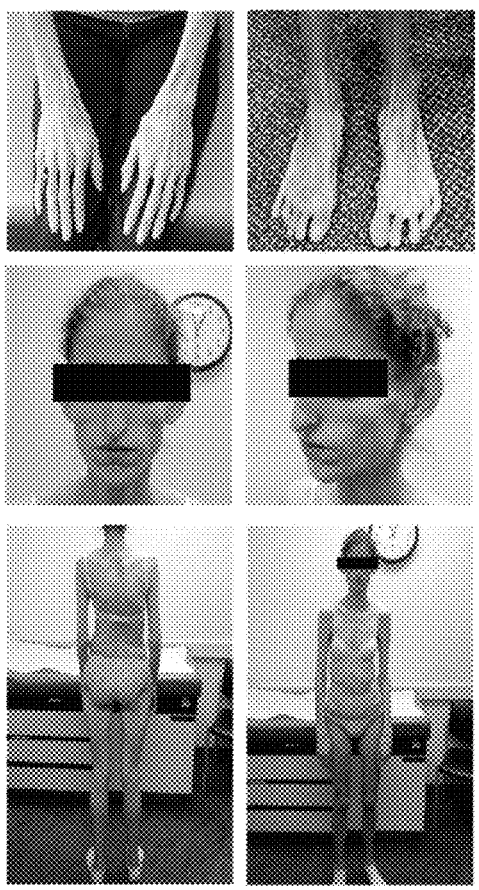

FIG. 1B

Patient 1 c.8207_8208insA
BMI = 9.9 kg/m$^2$

Patient 2 c.8226+1G>T
BMI = 13 kg/m$^2$

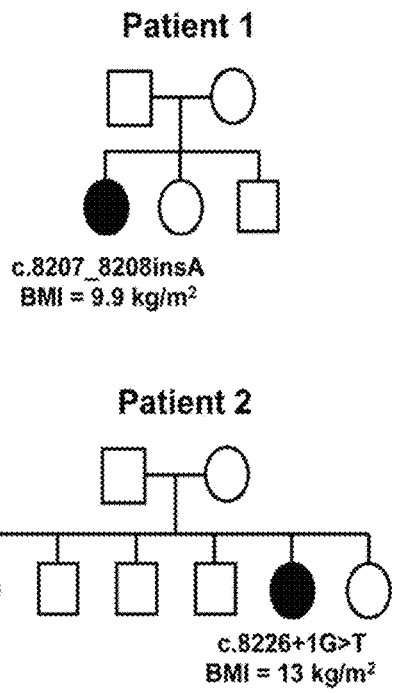

FIG. 1C

Patient 1: c.8207_8208ins1bp (penultimate exon)
Patient 2: c.8226+1G>T (ultimate intron)
Case 1: c.8135_8136del2bp (penultimate exon)
Case 2: c.8156_8175del20bp (penultimate exon)
Case 3: c.8226+1G>T (ultimate intron)
Case 4: c.8175_8182del8bp (penultimate exon)
Case 5: c.8226+1G>A (ultimate intron)

FIG. 1D

WT
2701 VSGEMDDNSLSPEACYECKINGYPKRGRKRRSTNETDASNIEDQSETEANVSLASWDVEK
2761 TAIFAFNISHVSNKVRILELLPALTTLTNHHNRYLIESGNEDGFFKINQKEGISYLHFTKK
2821 KPVAGTYSLQISSTPLYKKKELNQLEDKYDKDVLSGELGDNLKMKIQVLLH*

Patient #1
2701 VSGEMDDNSLSPEACYECKINGYPKRGRKRRSTNET*

Patient #2
2701 VSGEMDDNSLSPEACYECKINGYPKRGRKRRSTNETDASNIE...*

Case 1
2701 VSGEMDDNSLSPEACYEC...*

Case 2
2701 VSGEMDDNSLSPEACYEC...*

Case 3
2701 VSGEMDDNSLSPEACYECKINGYPKRGRKRRSTNETDASNIE...*

Case 4
2701 VSGEMDDNSLSPEACYECKINGYPK...*

Case 5
2701 VSGEMDDNSLSPEACYECKINGYPKRGRKRRSTNETDASNIE...*

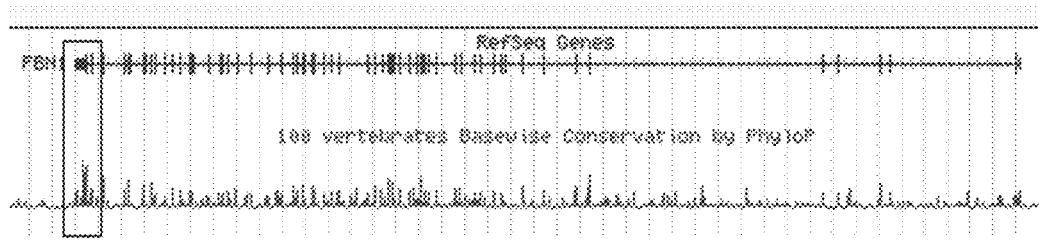
FIG. 3A
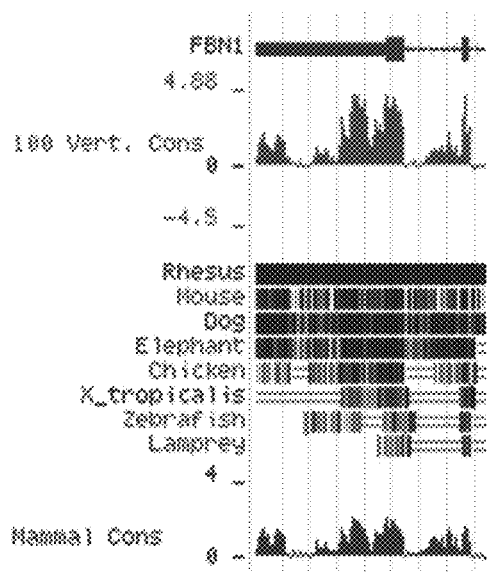
FIG. 3B
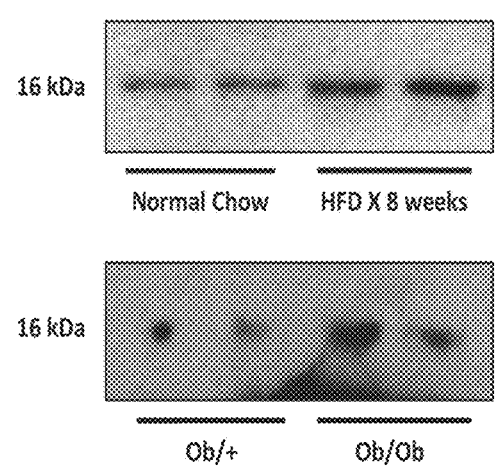
FIG. 3C Mice
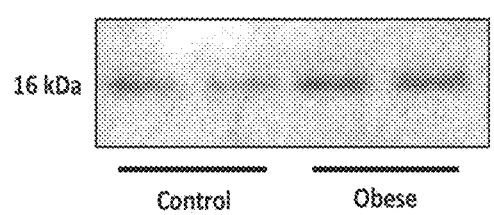
FIG. 3D Humans

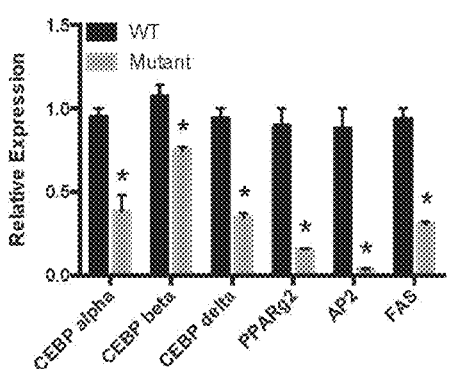
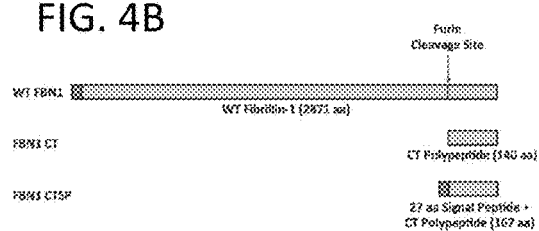
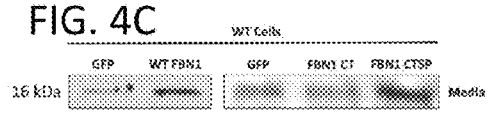
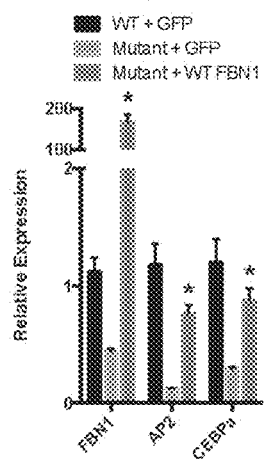
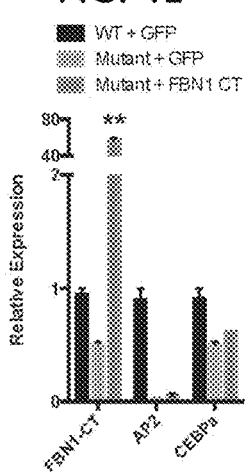
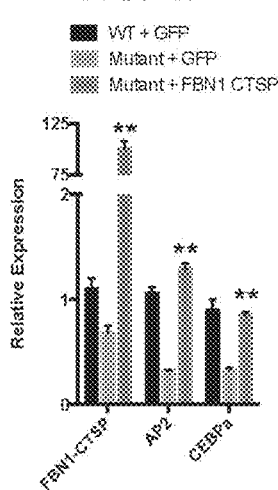
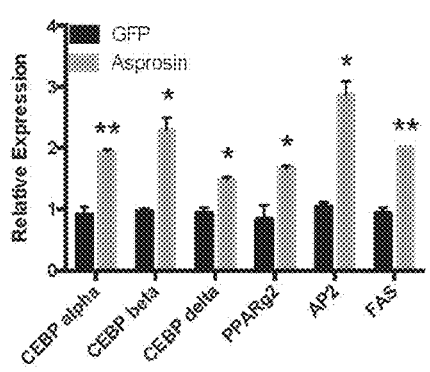
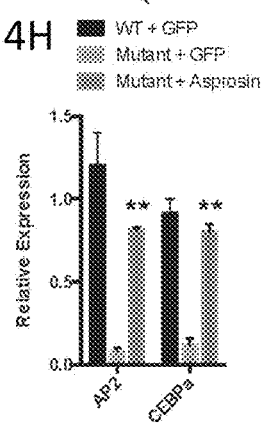

FIG. 5A
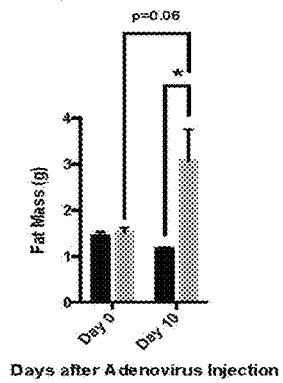
FIG. 5B
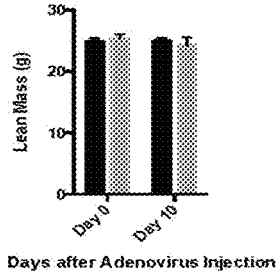
FIG. 5C
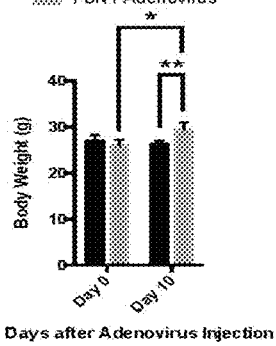
FIG. 5D
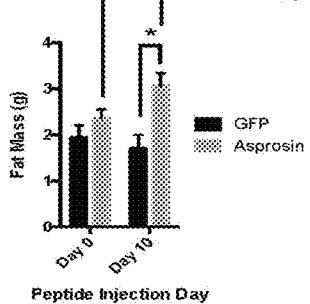
FIG. 5E
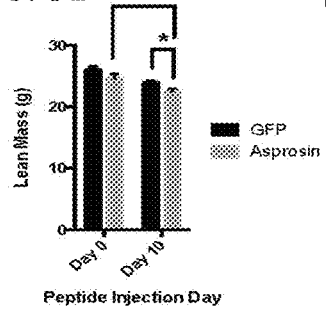
FIG. 5F
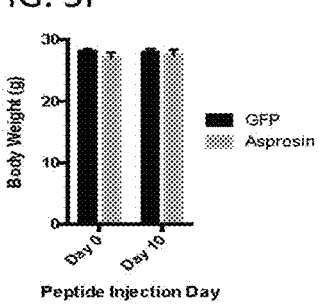
FIG. 5G
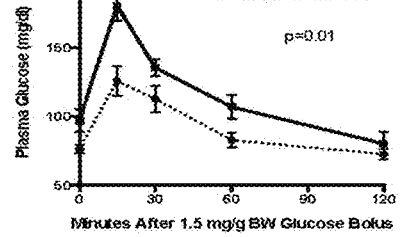
FIG. 5H
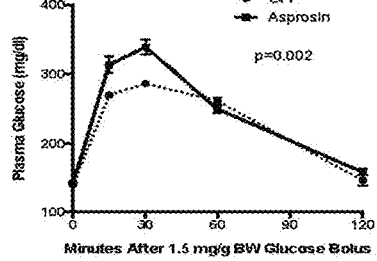
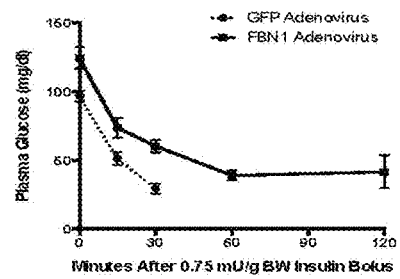
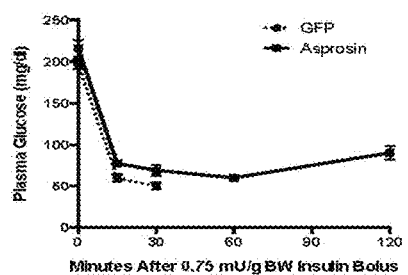
FIG. 4I
FIG. 4J FIG. 8A
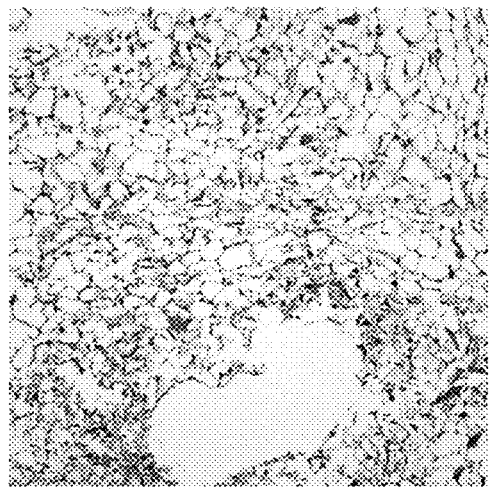
GFP Adenovirus
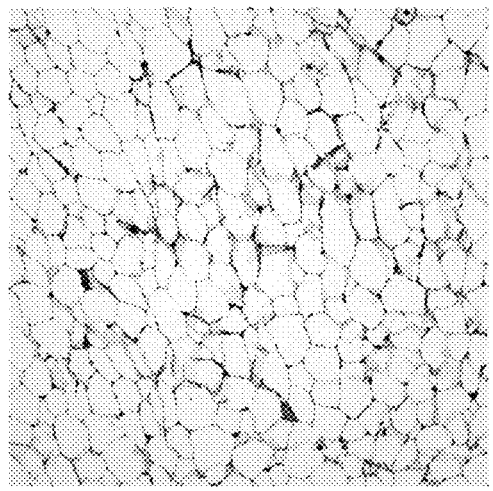
FBN1 Adenovirus
FIG. 8B
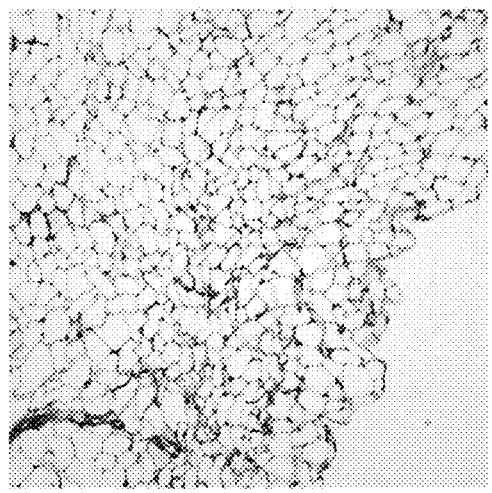
GFP
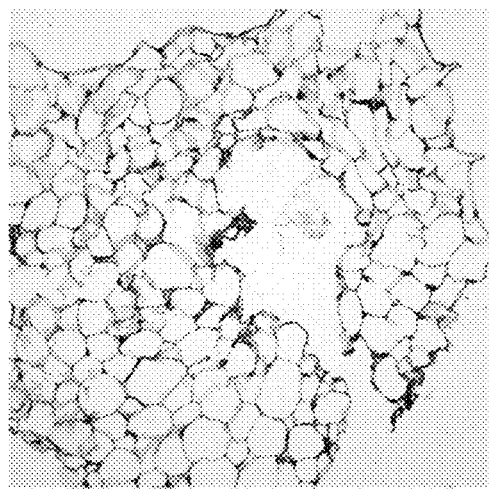
Asprosin FIG. 12A
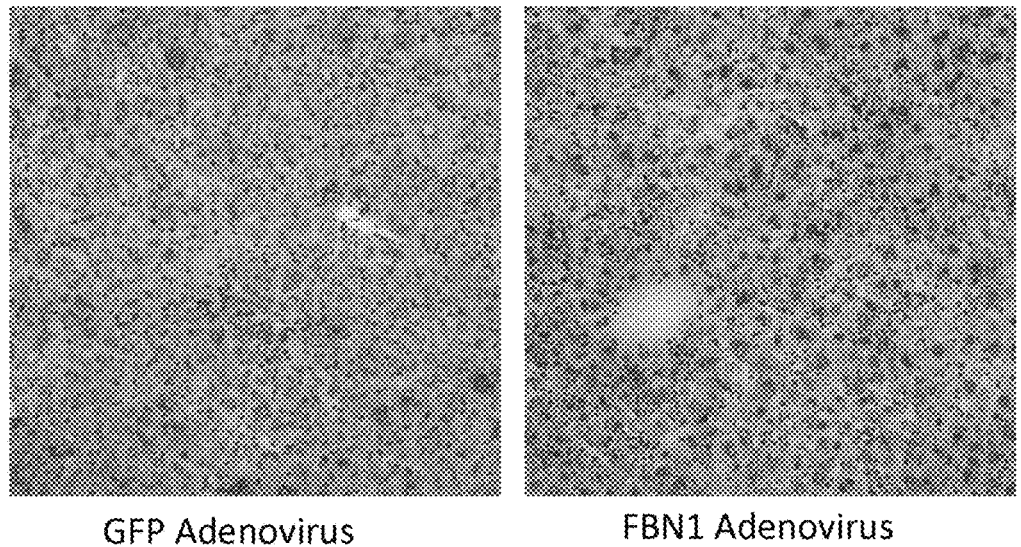
GFP Adenovirus   FBN1 Adenovirus
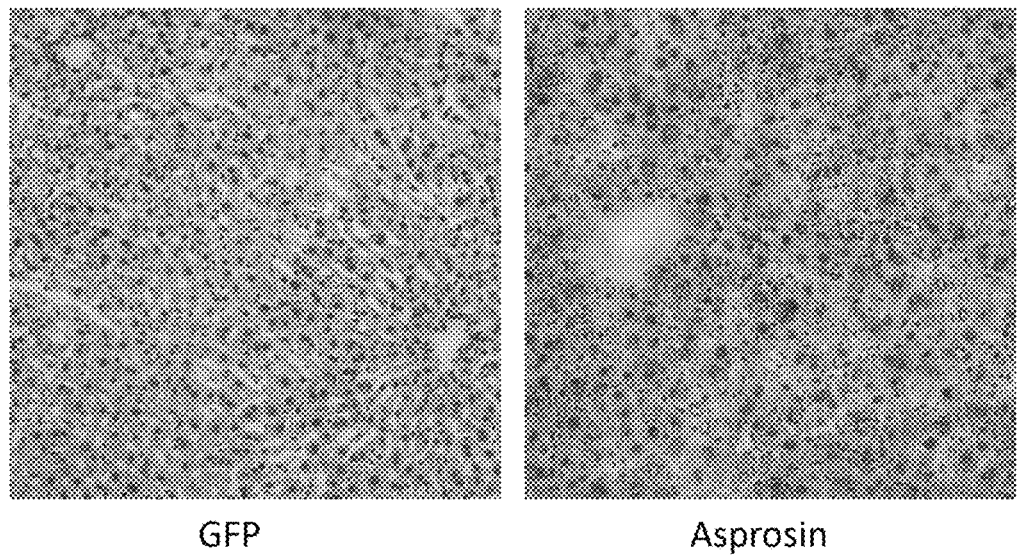
GFP   Asprosin
FIG. 12B 16 KD C-terminal Peptide →

METHODS FOR STIMULATION OF APPETITE AND INCREASE IN WEIGHT BY ADMINISTRATION OF ASPROSIN

This application is a national phase application under 35 U.S.C. § 371 that claims priority to International Application No. PCT/US2014/067162 filed Nov. 24, 2014, which claims priority to U.S. Provisional Application Ser. No. 61/910,498, filed Dec. 2, 2013, and to U.S. Provisional Application Ser. No. 62/010,557, filed Jun. 11, 2014, and to U.S. Provisional Application Ser. No. 62/037,779, filed Aug. 15, 2014, and to U.S. Provisional Application Ser. No. 62/073,501, filed Oct. 31, 2014, all of which applications are incorporated by reference herein in their entirety.

TECHNICAL FIELD

Embodiments of the disclosure include at least the fields of cell biology, molecular biology, endocrinology, and medicine.

BACKGROUND

The American Medical Association classified obesity as a disease in 2013 (Morgen & Sorenson, 2014), and as a leading preventable cause of death worldwide a clearer understanding of its genetic and molecular underpinnings has never been more important (Morgen & Sorenson, 2014; Malik, et al., 2013). Obesity is caused by an imbalance between energy intake and output (Spiegelman, et al., 2001; Spiegelman, et al., 1996). Because of the number of organs that impact these two processes and the complexity of energy homeostasis, the study of obesity remains a significant scientific challenge (Spiegelman, et al., 2001). Historically, study of extreme human variation has been a powerful tool for solving complex biological problems and for developing therapeutic targets against disease (Goldstein, et al., 2009; Friedman, et al., 2009). The present disclosure describes the loss of a new circulating polypeptide hormone responsible for maintenance of fat mass and associated glycemic control as the molecular mechanism driving the phenotype of an extreme thinness disorder in humans known as Neonatal Progeroid Syndrome (NPS) (Hou, et al., 2009; O'Neill, et al., 2007).

BRIEF SUMMARY

Embodiments of the disclosure concern methods and compositions that impact the weight of an individual, where certain compositions are useful to increase the weight of an individual and certain compositions are useful to decrease the weight of an individual. Although the loss or increase in weight may be by any suitable means, in specific embodiments the loss or increase in weight is because of the corresponding loss or increase of adipose mass. An individual that increases their weight may do so at least in part by increasing their appetite, although in certain embodiments their weight increases without increasing their appetite.

Embodiments of the disclosure include methods and compositions that encompass a C-terminal fragment of Fibrillin-1, referred to herein as asprosin, or functional fragments or functional derivatives thereof. The increase in asprosin, such as in circulating asprosin, is useful for increasing weight of an individual, whereas the decrease in asprosin is useful for decreasing weight of an individual, in particular embodiments.

In particular embodiments, asprosin or functional fragments or functional derivatives thereof are provided to an individual in need of gaining weight, including in need of gaining adipose mass. Such an individual may be in need of gaining weight because they have a medical condition that prevents them from gaining weight or retaining weight and/or because they cannot or do not gain or retain weight for other reasons, such as being naturally underweight or by external causes. In specific embodiments, the medical condition is because of one or more genetic defects in the individual. In certain embodiments, the medical condition comprises cachexia as a symptom.

In certain embodiments, an individual is in need of losing weight and is therefore provided an effective amount of an inhibitor of the native asprosin in the individual. The inhibitor may be of any kind, but in specific embodiments the inhibitor is an antibody or small molecule, including a small molecule that targets an epitope on the N-terminal end of asprosin, the C-terminal end of asprosin, or an internal region of asprosin, for example.

In embodiments of the disclosure, an individual is in need of an improvement of glucose control and is therefore provided an effective amount of an inhibitor of the native asprosin in the individual. The inhibitor may be of any kind, but in specific embodiments the inhibitor is an antibody or small molecule, including a small molecule that targets an epitope on the N-terminal end of asprosin, the C-terminal end of asprosin, or an internal region of asprosin, for example. Such an individual may be of any kind, but in specific embodiments, the individual is diabetic, pre-diabetic (either or which may be determined by the fasting plasma glucose test, the oral glucose tolerance test and/or the Hemoglobin A1C test), insulin-resistant, and so forth. In specific embodiments, hyperglycemics and insulin-resistant individuals are provided an effective amount of one or more asprosin inhibitors. In certain embodiments, an individual is provided an effective amount of an asprosin inhibitor when the individual is in need of an improvement in the control of blood sugar and the asprosin inhibitors is given to the individual specifically for such improvement.

Embodiments of the disclosure include an appetite stimulant that comprises asprosin or functional fragments or functional derivatives thereof. Embodiments of the disclosure also include an appetite suppressant that comprises one or more inhibitors of asprosin.

In one embodiment, there is a recombinant asprosin polypeptide or a functional derivative or functional fragment thereof. In a specific embodiment, the asprosin polypeptide comprises the sequence of SEQ ID NO:1. In particular embodiments, the polypeptide is comprised in a pharmaceutically acceptable carrier. In specific embodiments, the functional derivative or fragment thereof comprises 1, 2, 3, 4, 5, 6, 7, 8, 9, 10, 11, 12, 13, 14, 15, 16, 17, 18, 19, or 20 or more amino acid alterations compared to SEQ ID NO:1. The functional derivative or functional fragment thereof may comprise an N-terminal truncation of SEQ ID NO:1, in certain embodiments, and the truncation may be no more than 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids or wherein the truncation is at least 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids, in particular embodiments. In certain embodiments, the functional derivative or functional fragment thereof comprises a C-terminal truncation of SEQ ID NO:1, such as wherein the truncation is no more than 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids or is at least 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids, for example. In some embodiments, the functional derivative or functional fragment thereof comprises an internal deletion in SEQ ID NO:1, such as an internal deletion that is no more than 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids or is at least 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids, for example. In some cases, the asprosin functional derivative or fragment thereof may comprise sequence that is at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identical to SEQ ID NO:1. In specific embodiments, the polypeptide is labeled.

In one embodiment, there is a method of modulating the weight of an individual, comprising the step of modulating the level of native asprosin in the individual. In a specific embodiment, when the individual has insufficient weight, the level of native asprosin is increased. In a specific embodiment, when the individual has excessive weight, the level of native asprosin is decreased. In particular cases, the level of native asprosin is modulated by modulating transcription of asprosin and/or is modulated by modulating translation of asprosin. In specific embodiments, the level of native aspro sin is modulated by modulating secretion of asprosin from cells and/or is modulated by modulating the stability of asprosin.

In one embodiment, there is a method of increasing the weight of an individual, comprising the step of providing an effective amount of any polypeptide contemplated herein to the individual. In a specific embodiment, the appetite level of the individual is increased.

In one embodiment, there is a method of decreasing the weight of an individual, comprising the step of providing an effective amount of an inhibitor of asprosin to the individual. In a specific embodiment, the inhibitor is an antibody, although it may be a small molecule.

In one embodiment, there is a method of decreasing the level of glucose in the blood of an individual, comprising the step of providing an effective amount of an inhibitor of aspro sin to the individual.

In a particular embodiment, there is a method of increasing the level of glucose in the blood of an individual, comprising the step of providing an effective amount of any polypeptide as contemplated herein to the individual.

In an embodiment, there is a kit comprising any polypeptide as contemplated herein, wherein the polypeptide is housed in a suitable container.

In one embodiment, there is a method of stimulating the appetite of an individual, comprising the step of providing an effective amount of any polypeptide contemplated herein to the individual.

In a certain embodiment, there is an inhibitor of any polypeptide as contemplated herein.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

FIG. 1A-1D: Neonatal progeroid syndrome results from de novo, heterozygous, truncating mutations at the 3' end of FBN1—1A, Representative images of two NPS patients showing the associated lipodystrophy, which predominantly affects the face and extremities while sparing the gluteal area. 1B, FBN1 mutations, body mass indices (BMI) and family pedigrees of two NPS patients. 1C, 3' FBN1 mutations in the two NPS patients of the disclosure and five NPS patients from published case reports. Patient #2 also has a heterozygous missense mutation (c.8222T>C) in FBN1 that is predicted to be benign and is not indicated in the figure for clarity. 1D, All seven NPS mutations are clustered around the Furin cleavage site (RGRKRR motif (SEQ ID NO:5) shown in red) and are predicted to result in heterozygous ablation of all of, or the majority of, the C-terminal polypeptide, which is shown in black following the RGRKRR motif. (SEQ ID NO:5). Non-native amino acids added on due to frame-shift are shown in blue. A wild type (WT) sequence is presented for reference.

FIG. 3A-3D: Asprosin is a highly conserved, circulating, C-terminal cleavage product of Fibrillin-1—3A, Human FBN1 gene and its evolutionary conservation are depicted using the UCSC genome browser. The Asprosin coding region is boxed. 3B, A zoomed in view of exons 65 and 66, which contribute to the Asprosin coding region, is depicted using the UCSC genome browser. 3C, Western blot analysis targeted against Asprosin was performed on plasma from 14 week old WT mice subjected to normal chow or 8 weeks of high fat diet, or from 8 week old male mice either heterozygous or homozygous for the spontaneous Leptin mutation known as ob. 3D, Western blot analysis targeted against Asprosin was performed on plasma from obese humans or normal weight control subjects.

FIG. 4A-4H: Asprosin rescues the NPS associated adipogenic differentiation defect in vitro—4A, Expression of several early and late markers of adipogenesis was measured by quantitative polymerase chain reaction in human dermal fibroblasts from NPS patients (mutant) or unaffected control subjects (WT) that were subjected to adipogenic differentiation for 7 days. 4B, Animated depictions of expression constructs expressing WT fibrillin-1 (WT FBN1), Asprosin without a signal peptide (FBN1 CT), and Asprosin with an attached signal peptide (FBN1 CTSP), all under control of the CMV promoter. The 27 amino acid native fibrillin-1 signal peptide is shown in red. 4C, Western blot analysis targeted against Asprosin was performed on cell culture media from WT human dermal fibroblasts exposed to adipogenic induction for 7 days and concurrently exposed to expression constructs driving WT fibrillin-1 (WT FBN1), Asprosin without a signal peptide (FBN1 CT), and Asprosin with an attached signal peptide (FBN1 CTSP), or Green Fluorescent Protein (GFP) as a control. 4D, Expression of an early (CEBPα) and a late (AP2) marker of adipogenesis was measured by quantitative polymerase chain reaction in human dermal fibroblasts from NPS patients (mutant) or unaffected control subjects (WT) that were subjected to adipogenic differentiation for 7 days, while concurrently exposed to expression constructs driving WT fibrillin-1 (WT FBN1) or GFP. Statistical comparison is shown between the Mutant+GFP group and the Mutant+WT FBN1 group. 4E, Expression of an early (CEBPα) and a late (AP2) marker of adipogenesis was measured by quantitative polymerase chain reaction in human dermal fibroblasts from NPS patients (mutant) or unaffected control subjects (WT) that were subjected to adipogenic differentiation for 7 days, while concurrently exposed to expression constructs driving Asprosin without a signal peptide (FBN1 CT) or GFP. Statistical comparison is shown between the Mutant+GFP group and the Mutant+FBN1 CT group. 4F, Expression of an early (CEBPα) and a late (AP2) marker of adipogenesis was measured by quantitative polymerase chain reaction in human dermal fibroblasts from NPS patients (mutant) or unaffected control subjects (WT) that were subjected to adipogenic differentiation for 7 days, while concurrently exposed to expression constructs driving Asprosin with an attached signal peptide (FBN1 CTSP) or GFP. Statistical comparison is shown between the Mutant+GFP group and the Mutant+FBN1 CTSP group. 4G, Expression of several early and late markers of adipogenesis was measured by quantitative polymerase chain reaction in human dermal fibroblasts from unaffected control subjects (WT) that were subjected to adipogenic differentiation for 7 days, while concurrently exposed to 60 nanomolar recombinant Asprosin or GFP. Induction of CEBPα expression was observed with a range of Asprosin doses from 30 nanomolar to 625 nanomolar. 4H, Expression of an early (CEBPα) and a late (AP2) marker of adipogenesis was measured by quantitative polymerase chain reaction in human dermal fibroblasts from NPS patients (mutant) or unaffected control subjects (WT) that were subjected to adipogenic differentiation for 7 days, while concurrently exposed to 60 nanomolar recombinant Asprosin or GFP. Data are represented as the mean±SEM. Unpaired student's t test was used for evaluation of statistical significance. *$P<0.05$, $P<0.01$, and *$P<0.001$.

FIG. 5A-5J: High circulating Asprosin is obesogenic and diabetogenic—5A, 5B, 5C, Fat mass and lean mass using Magnetic Resonance Imaging (MRI), and total body weight were measured in WT mice subjected to a one-time tail vein injection of $10^{11}$ viral particles of adenovirus carrying cDNA (under control of the CMV promoter) for FBN1 or GFP (n=6 in each group). Measurements were conducted on the indicated days. 5D, 5E, 5F, Fat mass and lean mass using Magnetic Resonance Imaging (MRI), and total body weight were measured in WT mice subjected to daily subcutaneous injection of 2.6 micro molar recombinant Asprosin or GFP for 10 days (n=6 in each group). Measurements were conducted on the indicated days. 5G, 5I, Glucose tolerance test and insulin tolerance test were performed on fasted WT mice subjected to a one-time tail vein injection of $10^{11}$ viral particles of adenovirus carrying cDNA (under control of the CMV promoter) for FBN1 or GFP (n=6 in each group). Measurements were conducted 10 days after the adenoviral injection. 5H, 5J, Glucose tolerance test and insulin tolerance test were performed on fasted WT mice subjected to daily subcutaneous injection of 2.6 micro molar recombinant Asprosin or GFP for 10 days (n=6 in each group). Measurements were conducted 10 days after the initial injection. Of note, insulin tolerance test on the GFP mice (both adenovirus and peptide mediated delivery) was complicated by severe hypoglycemia at the 60 minute mark that manifested as a "too low to measure" value on the glucometer. Those mice had to be injected with exogenous glucose to prevent fatal hypoglycemia. FBN1 adenovirus and Asprosin injected mice however maintained their blood glucose levels as indicated in the figure. Data are represented as the mean±SEM. For evaluation of statistical significance, unpaired student's t test was used when comparing two groups, or ANOVA was used when comparing more than two groups. *$P<0.05$, $P<0.01$, and *$P<0.001$.

FIG. 8A-8B: Higher circulating Asprosin results in increased fat cell size—8A, Formalin-fixed inguinal white adipose tissue sections were stained with hematoxylin and eosin from 4-hour fasted WT mice subjected to a one-time tail vein injection of $10^{11}$ viral particles of adenovirus carrying cDNA (under control of the CMV promoter) for FBN1 or GFP. Sections were taken 10 days after the adenoviral injection. 8B, Formalin-fixed inguinal white adipose tissue sections were stained with hematoxylin and eosin from 4-hour fasted WT mice subjected to daily subcutaneous injection of 2.6 micro molar recombinant Asprosin or GFP for 10 days. Sections were taken 10 days after the adenoviral injection.

FIG. 12A-12B: Higher circulating Asprosin results in increased hepatic lipid accumulation—12A, Formalin-fixed liver sections were stained with hematoxylin and eosin, and Oil-Red-O stain for neutral lipid, from 4-hour fasted WT mice subjected to a one-time tail vein injection of $10^{11}$ viral particles of adenovirus carrying cDNA (under control of the CMV promoter) for FBN1 or GFP. Sections were taken 10 days after the adenoviral injection. 12B, Formalin-fixed liver sections were stained with hematoxylin and eosin, and Oil-Red-O stain for neutral lipid, from 4-hour fasted WT mice subjected to daily subcutaneous injection of 2.6 micro molar recombinant Asprosin or GFP for 10 days. Sections were taken 10 days after the adenoviral injection.

DETAILED DESCRIPTION

Figure 2A:
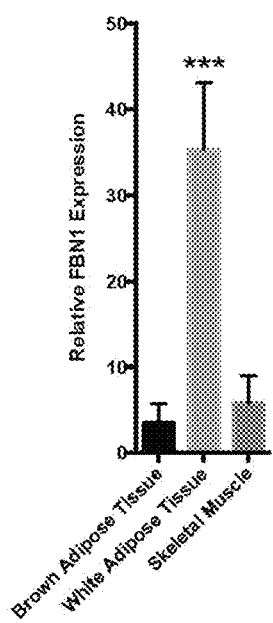
FIG. 2A-2C: FBN1 is highly and dynamically expressed in white adipose tissue—2A, FBN1 expression was measured by quantitative polymerase chain reaction in mouse white adipose tissue, brown adipose tissue and skeletal muscle (n=5 in each group). 2B, FBN1 expression was measured by quantitative polymerase chain reaction in human pre-adipocytes that were subjected to adipogenic differentiation for 7 days. CEBPα expression is shown as a marker of adipogenic differentiation. 2C, FBN1 expression was measured by quantitative polymerase chain reaction in inguinal white adipose tissue from male, WT mice subjected to normal chow or 10 weeks of high fat diet (n=5 in each group). Data are represented as the mean±SEM. Unpaired student's t test was used for evaluation of statistical significance. *P<0.05, P<0.01, and *P<0.001.

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein embodiments which are disclosed and still obtain a like or similar result without departing from the spirit and scope of the invention.

I. Asprosin

Embodiments of the disclosure include methods and compositions related to asprosin, which is a C-terminal cleavage fragment of fibrillin-1. A sequence of native human asprosin (amino acids 2732-2871 of fibrillin-1; SEQ ID NO:1) is as follows: STNETDASNIEDQSETEANVSLAS-WDVEKTAIFAFNISHVSNKVRILELLPALTTLTNHNR YLIESGNEDGFFKINQKEGISYLHFTKKKPVAGTYS-LQISSTPLYKKKELNQLEDKYDKD YLSGELGDNLK-MKIQVLLH. Asprosin may be isolated from human cells, and therefore no longer residing in nature, or it may be recombinant, in certain embodiments. As referred to herein, when the native sequence of SEQ ID NO:1 is generated by recombinant means, the resultant polypeptide may be referred to as a recombinant asprosin. A sequence of another example of a recombinant asprosin includes a label or tag. As an example, a His tag attached at N-terminus along with a methionine to include a start codon for translation in E. coli (SEQ ID NO:2) is as follows: MHHHHHHSTNETDAS-NIEDQSETEANVSLASWDVEKTAIFAFNISHVSNK-VRILELLPAL TTLTNHNRYLIESGNEDGFFKINQKEGI-SYLHFTKKKPVAGTYSLQIS STPLYKKKELNQL EDKYDKDYLSGELGDNLKMKIQVLLH. Embodiments of asprosin include functional derivatives or functional fragments thereof, and the derivative or fragment may be considered functional if it has the ability to have a mammalian individual increase appetite and/or gain weight when provided an effective amount. Such an activity may be measured by any suitable means, including MRI scans to assess increase in adipose mass or measurements of body weight using a weighing scale, for example. In particular embodiments, one can assess functional activity by assaying for promotion of adipocyte differentiation in vitro, for example. In specific embodiments, the asprosin or functional fragment or functional derivative is soluble. The asprosin or functional fragment or functional derivative may be comprised in a fusion protein.

Asprosin proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. An asprosin coding region (such as within fibrillin-1, although it may be separated from fibrillin-1) may be amplified and/or expressed using the techniques disclosed herein or as would be known to those of ordinary skill in the art. Alternatively, various commercial preparations of proteins, polypeptides and peptides are known to those of skill in the art.

In certain embodiments an asprosin (or fragment or derivative thereof) proteinaceous compound may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide. Biological functional equivalents of asprosin, including such derivatives and fragments, may be employed. As modifications and/or changes may be made in the structure of asprosin polynucleotides and and/or proteins according to the present invention, while obtaining molecules having similar or improved characteristics, such biologically functional equivalents are also encompassed within the present invention.

An asprosin functional derivative or fragment thereof may comprise 1, 2, 3, 4, 5, 6, 7, 8, 9, 10, 11, 12, 13, 14, 15, 16, 17, 18, 19, or 20 or more amino acid alterations compared to SEQ ID NO:1. The asprosin functional derivative or fragment thereof may comprise an N-terminal truncation of SEQ ID NO:1, for example wherein the truncation is no more than 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids or wherein the truncation is at least 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids. The asprosin functional derivative or fragment thereof may comprise a C-terminal truncation of SEQ ID NO:1, such as wherein the truncation is no more than 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids or is at least 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids. The asprosin functional derivative or fragment thereof may comprise an internal deletion in SEQ ID NO:1, such as wherein the internal deletion is no more than 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids or is at least 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids. In specific embodiments, an asprosin functional derivative or fragment thereof may comprise sequence that is at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identical to SEQ ID NO:1.

In specific embodiments, an appetite stimulant comprises asprosin or a functional fragment or functional derivative. The stimulant may be specifically formulated with asprosin to stimulate the appetite of a mammalian individual. Such a stimulant may be provided to an individual that is underweight, undernourished, underfed, that is trying to build up mass, to increase mass of agricultural animals (such as cows, pigs, lambs, chickens, etc.), for bodybuilders, and so forth. The stimulant composition may have other stimulants than asprosin.

A. Modified Polynucleotides and Polypeptides

A biological functional equivalent of asprosin may be produced from a polynucleotide that has been engineered to contain distinct sequences while at the same time retaining the capacity to encode the "wild-type" or standard protein. This can be accomplished to the degeneracy of the genetic code, i.e., the presence of multiple codons, which encode for the same amino acids. In one example, one of skill in the art may wish to introduce a restriction enzyme recognition sequence into a polynucleotide while not disturbing the ability of that polynucleotide to encode a protein.

In another example, an asprosin polynucleotide made be (and encode) a biological functional equivalent with more significant changes. Certain amino acids may be substituted for other amino acids in a protein structure without appreciable loss of interactive binding capacity with structures such as, for example, antigen-binding regions of antibodies, binding sites on substrate molecules, receptors, and such like. So-called "conservative" changes do not disrupt the biological activity of the protein, as the structural change is not one that impinges of the protein's ability to carry out its designed function. It is thus contemplated by the inventors that various changes may be made in the sequence of genes and proteins disclosed herein, while still fulfilling the goals of the present invention.

In terms of functional equivalents, it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Biologically functional equivalents are thus defined herein as those proteins (and polynucleotides) in selected amino acids (or codons) may be substituted.

In general, the shorter the length of the molecule, the fewer changes that can be made within the molecule while retaining function. Longer domains may have an intermediate number of changes. The full-length protein will have the most tolerance for a larger number of changes. However, it must be appreciated that certain molecules or domains that are highly dependent upon their structure may tolerate little or no modification.

Amino acid substitutions are generally based on the relative similarity of the amino acid side-chain substituents, for example, their hydrophobicity, hydrophilicity, charge, size, and/or the like. An analysis of the size, shape and/or type of the amino acid side-chain substituents reveals that arginine, lysine and/or histidine are all positively charged residues; that alanine, glycine and/or serine are all a similar size; and/or that phenylalanine, tryptophan and/or tyrosine all have a generally similar shape. Therefore, based upon these considerations, arginine, lysine and/or histidine; alanine, glycine and/or serine; and/or phenylalanine, tryptophan and/or tyrosine; are defined herein as biologically functional equivalents.

To effect more quantitative changes, the hydropathic index of amino acids may be considered. Each amino acid has been assigned a hydropathic index on the basis of their hydrophobicity and/or charge characteristics, these are: isoleucine (+4.5); valine (+4.2); leucine (+3.8); phenylalanine (+2.8); cysteine/cystine (+2.5); methionine (+1.9); alanine (+1.8); glycine (0.4); threonine (0.7); serine (0.8); tryptophan (0.9); tyrosine (1.3); proline (1.6); histidine (3.2); glutamate (3.5); glutamine (3.5); aspartate (3.5); asparagine (3.5); lysine (3.9); and/or arginine (4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index and/or score and/or still retain a similar biological activity. In making changes based upon the hydropathic index, the substitution of amino acids whose hydropathic indices are within ±2 is preferred, those which are within ±1 are particularly preferred, and/or those within ±0.5 are even more particularly preferred.

It also is understood in the art that the substitution of like amino acids can be made effectively on the basis of hydrophilicity, particularly where the biological functional equivalent protein and/or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and/or antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (0.4); proline (−0.5±1); alanine (0.5); histidine (0.5); cysteine (1.0); methionine (1.3); valine (1.5); leucine (1.8); isoleucine (1.8); tyrosine (2.3); phenylalanine (2.5); tryptophan (3.4). In making changes based upon similar hydrophilicity values, the substitution of amino acids whose hydrophilicity values are within ±2 is preferred, those which are within ±1 are particularly preferred, and/or those within ±0.5 are even more particularly preferred.

B. Altered Amino Acids

The present invention, in many aspects, relies on the synthesis of peptides and polypeptides in cyto, via transcription and translation of appropriate polynucleotides. These peptides and polypeptides will include the twenty "natural" amino acids, and post-translational modifications thereof. However, in vitro peptide synthesis permits the use of modified and/or unusual amino acids. Exemplary, but not limiting, modified and/or unusual amino acids are known in the art.

C. Mimetics

In addition to the biological functional equivalents discussed above, the present inventors also contemplate that structurally or functionally similar compounds may be formulated to mimic the key portions of peptide or polypeptides of the present invention. Such compounds, which may be termed peptidomimetics, may be used in the same manner as the peptides of the invention and, hence, also are functional equivalents. In specific embodiments, the mimetic comprises one or more beta pleats from asprosin.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule. Such peptidomimetics include compounds that do not incorporate any natural amino acids or amino acid side chains, but are designed based on the asprosin peptide sequence and have the ability to functionally replace asprosin.

II. Inhibitors of Asprosin or of the Asprosin Receptor

Embodiments of the disclosure include one or more inhibitors of asprosin. In specific embodiments, the inhibitor is an antibody, although in some cases the inhibitor is not an antibody. In specific embodiments, the inhibitor may be one or more small molecules, one or more aptamers, one or more non-antibody phage display-derived peptides, a combination thereof, and so forth. In specific embodiment, an inhibitor of asprosin specifically binds and inactivates asprosin. In specific embodiments, the inhibitor is soluble. In some embodiments, there are methods and compositions for soluble receptor-mediated inhibition of asprosin. In particular embodiments, RNAi- and/or microRNA-mediated inhibition may be employed, for example in particular embodiments wherein aspro sin has its own transcriptional unit separate from FBN1.

Embodiments of the disclosure include one or more inhibitors of the asprosin receptor(s). In specific embodiments, the inhibitor is an antibody, although in some cases the inhibitor is not an antibody. In specific embodiments, the inhibitor may be one or more small molecules, one or more aptamers, one or more non-antibody phage display-derived peptides, RNAi or microRNA mediated inhibitors, specific inhibitors of its downstream signaling, or a combination thereof, and so forth. In specific embodiment, an inhibitor of the asprosin receptor specifically binds and inactivates asprosin. In one specific embodiment it specifically blocks its expression or otherwise decreases its functional activity. In specific embodiments, the inhibitor is soluble.

In specific embodiments, the inhibitor targets a structural or functional motif, and the asprosin target site of the inhibitor may or may not be known. In specific embodiments, the inhibitor targets one or more beta pleats from asprosin. In specific embodiments, the inhibitor of asprosin is an inhibitor of the receptor for asprosin.

In certain embodiments, there is an appetite suppressant that comprises one or more asprosin inhibitors. The suppressant composition may have other suppressants than asprosin. The suppressant may be specifically formulated with asprosin to suppress the appetite of a mammalian individual. Such a suppressant may be provided to an individual that is overweight, obese, has diabetes, is at risk for becoming overweight, is at risk for becoming obese, and so forth.

In particular embodiments, the inhibitor is an antibody. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

A. Polyclonal Antibodies

Polyclonal antibodies to asprosin generally may be raised in animals by multiple subcutaneous (sc) or intraperitoneal (ip) injections of asprosin or a fragment thereof and an adjuvant. It may be useful to conjugate the asprosin or a fragment containing the target amino acid sequence to a protein that is immunogenic in the species to be immunized, e.g. keyhole limpet hemocyanin, serum albumin, bovine thyroglobulin, or soybean tryp sin inhibitor using a bifunctional or derivatizing agent, for example maleimidobenzoyl sulfosuccinimide ester (conjugation through cysteine residues), N-hydroxysuccinimide (through lysine residues), glytaraldehyde, succinic anhydride, $SOCl_2$, or $R^1$ N=C=NR, where R and $R^1$ are different alkyl groups.

Animals may be immunized against the immunogenic conjugates or derivatives by combining 1 mg of 1 µg of conjugate (for rabbits or mice, respectively) with 3 volumes of Freud's complete adjuvant and injecting the solution intradermally at multiple sites. One month later the animals are boosted with 1/5 to 1/10 the original amount of conjugate in Freud's complete adjuvant by subcutaneous injection at multiple sites. 7 to 14 days later the animals are bled and the serum is assayed for anti-asprosin antibody titer. Animals are boosted until the titer plateaus. Preferably, the animal boosted with the conjugate of the same asprosin, but conjugated to a different protein and/or through a different cross-linking reagent. Conjugates also can be made in recombinant cell culture as protein fusions. Also, aggregating agents such as alum are used to enhance the immune response.

B. Monoclonal Antibodies

In specific embodiments, monoclonal antibodies may be generated and employed as inhibitors of asprosin for the use of losing weight in an individual. The immunogen for the monoclonal antibodies may be the entire asprosin polypeptide or may be a fragment thereof. Exemplary sequences of immunogens that may be employed for the generation of monoclonal antibodies are as follows:

```
                                     (SEQ ID NO: 3)
HuFbn1-2746:2770   ETEANVSLASWDVEKTAIFAFNISH (SEQ ID NO: 4)
HuFbn1 2838:2865   KKKELNQLEDKYDKDYLSGELGDNLKMK
```

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, the anti-asprosin monoclonal antibodies of the invention may be made using the hybridoma method first described by Kohler & Milstein, Nature 256:495 (1975), or may be made by recombinant DNA methods [Cabilly, et al., U.S. Pat. No. 4,816,567]. In the hybridoma method, a mouse or other appropriate host animal, such as hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell [Goding, Monoclonal Antibodies: Principles and Practice, pp. 59-103 (Academic Press, 1986)].

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA.

Culture medium in which hybridoma cells are growing is assayed for production of monoclonal antibodies directed against asprosin. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson & Pollard, Anal. Biochem. 107:220 (1980).

After hybridoma cells are identified that produce antibodies of the desired specificity, affinity, and/or activity, the clones may be subcloned by limiting dilution procedures and grown by standard methods. Goding, Monoclonal Antibodies: Principles and Practice, pp. 59-104 (Academic Press, 1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., Proc. Nat. Acad. Sci. 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-asprosin monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for asprosin and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically may be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; biotin; radioactive isotopic labels, such as, e.g., $^{125}I$, $^{32}P$, $^{14}C$, or $^3H$, or an enzyme, such as alkaline phosphatase, beta-galactosidase or horseradish peroxidase.

Any method known in the art for separately conjugating the antibody to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982).

The antibodies of the present invention may be employed in any known assay method, such as competitive binding assays, direct and indirect sandwich assays, and immunoprecipitation assays. Zola, Monoclonal Antibodies: A Manual of Techniques, pp. 147-158 (CRC Press, Inc., 1987).

Competitive binding assays rely on the ability of a labeled standard (which may be an asprosin or an immunologically reactive portion thereof) to compete with the test sample analyte (asprosin) for binding with a limited amount of antibody. The amount of asprosin in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David & Greene, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

C. Humanized Antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature 321, 522-525 (1986); Riechmann et al., Nature 332, 323-327 (1988); Verhoeyen et al., Science 239, 1534-1536 (1988)], by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed Aug. 21, 1992, which is a continuation-in-part of application Ser. No. 07/715,272 filed Jun. 14, 1991.

D. Human Antibodies

Human monoclonal antibodies can be made by the hybridoma method. Human myeloma and mouse-human heteromyeloma cell lines for the production of human monoclonal antibodies have been described, for example, by Kozbor, J. Immunol. 133, 3001 (1984), and Brodeur, et al., Monoclonal Antibody Production Techniques and Applications, pp. 51-63 (Marcel Dekker, Inc., New York, 1987).

It is now possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region (J.sub.H) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., Proc. Natl. Acad. Sci. USA 90, 2551-255 (1993); Jakobovits et al., Nature 362, 255-258 (1993).

Alternatively, the phage display technology (McCafferty et al., Nature 348, 552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle.

Because the filamentous particle contains a single-stranded DNA copy of the phage genome, selections based on the functional properties of the antibody also result in selection of the gene encoding the antibody exhibiting those properties. Thus, the phage mimicks some of the properties of the B-cell. Phage display can be performed in a variety of formats; for their review see, e.g. Johnson, Kevin S. and Chiswell, David J., Current Opinion in Structural Biology 3, 564-571 (1993). Several sources of V-gene segments can be used for phage display. Clackson et al., Nature 352, 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222, 581-597 (1991), or Griffith et al., EMBO J. 12, 725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., Bio/Technol. 10, 779-783 [1992]). In this method, the affinity of "primary" human antibodies obtained by phage display can be improved by sequentially replacing the heavy and light chain V region genes with repertoires of naturally occurring variants (repertoires) of V domain genes obtained from unimmunized donors. This techniques allows the production of antibodies and antibody fragments with affinities in the nM range. A strategy for making very large phage antibody repertoires (also known as "the mother-of-all libraries") has been described by Waterhouse et al., Nucl. Acids Res. 21, 2265-2266 (1993), and the isolation of a high affinity human antibody directly from such large phage library is reported by Griffith et al., EMBO J. (1994), in press. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT patent application WO 93/06213, published Apr. 1, 1993). Unlike traditional humanization of rodent antibodies by CDR grafting, this technique provides completely human antibodies, which have no framework or CDR residues of rodent origin.

E. Bispecific Antibodies

Bispecific antibodies are monoclonal, preferably human or humanized, antibodies that have binding specificities for at least two different antigens. In the present case, one of the binding specificities is for asprosin, the other one is for any other antigen, and preferably for another receptor or receptor subunit. For example, bispecific antibodies specifically binding asprosin and an asprosin receptor or two different asprosin receptors are within the scope of the present invention.

Methods for making bispecific antibodies are known in the art. Traditionally, the recombinant production of bispecific antibodies is based on the coexpression of two immunoglobulin heavy chain-light chain pairs, where the two heavy chains have different specificities (Millstein and Cuello, Nature 305, 537-539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published May 13, 1993), and in Traunecker et al., EMBO 10, 3655-3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in copending application Ser. No. 07/931,811 filed Aug. 17, 1992.

For further details of generating bispecific antibodies see, for example, Suresh et al., Methods in Enzymology 121, 210 (1986).

F. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

III. Individuals in Need of Weight Gain

Embodiments of the disclosure include methods and compositions for increasing weight in an individual in need of weight gain. The individual may be in need of an increase in adipose mass, for example. The individual may be in need of weight gain for a variety of reasons, including because of a medical condition or state or for another reason. In cases wherein the individual is underweight because of a medical condition, the medical condition may or may not be a genetic condition or may or may not be an inherited condition. The cause of being underweight may be because of genetics, metabolism, and/or illness, in specific embodiments. In specific embodiments, the medical condition has being underweight as a symptom. In some cases, the symptom of being underweight is present in all individuals with the medical condition, although it may be present in less than all individuals with the medical condition. The symptom of being underweight may be because of a defect in pathways related to adipose metabolic regulation, fat storage, and inflammatory processes, although in some cases being underweight is not directly related to adipose metabolic regulation, fat storage, and inflammatory processes. The individual may be underweight because of Neonatal Progeroid Syndrome, Marfan Syndrome, HIV infection, hyperthyroidism, cancer, tuberculosis, gastrointestinal or liver problems, medicine side effect, or mental illness, such as those with anorexia nervosa or bulimia nervose, in some cases. For example, an individual that has cachexia may be subjected to methods and compositions of the disclosure. The cachexia may be the result of any reason, including, for example, from cancer, AIDS, chronic obstructive lung disease, multiple sclerosis, congestive heart failure, tuberculosis, familial amyloid polyneuropathy, mercury poisoning, hormonal deficiency, and so forth.

In specific embodiments, an individual in need of weight gain is an individual with a body mass index (BMI) of under 18.5 or a weight 15% to 20% below that normal for their age and height group. The individual that is subjected to methods and compositions of the disclosure may first be identified by a medical practitioner as being in need of weight gain, and the therapeutic composition may be delivered to the individual for the specific purpose of increasing weight.

IV. Treatment of Individuals in Need of Weight Gain

In embodiments of the disclosure an individual is determined to be in need of weight gain, such as by measuring their weight and/or by measuring their BMI and/or having an MRI and/or dual-energy x-ray absorptiometry (DEXA) scans for measurement of adipose mass. The individual may be known to be in need of weight gain or suspected of being in need of weight gain or at risk for being in need of weight gain. An individual may determine themselves that they are in need of weight gain and/or it may be determined by a suitable medical practitioner.

Once the individual is known to be in need of weight gain or known to be at risk or susceptible to being in need of weight gain, they may be given a suitable and effective amount of asprosin or a functional derivative or a functional fragment. In specific embodiments, one or more of asprosin or a functional derivative or a functional fragment are provided to the individual, such as in a composition or in multiple compositions. A composition comprising asprosin or a functional derivative or a functional fragment may be specifically formulated for a therapeutic application.

An individual may be provided suitable dose(s) of asprosin on an as needed basis or as part of a routine regimen. The individual may also be taking other measures and/or compositions to gain weight in addition to taking asprosin or a functional derivative or a functional fragment. The individual may take asprosin or a functional derivative or a functional fragment on a daily basis, weekly basis, monthly basis, and so on. The individual may take asprosin or a functional derivative or a functional fragment with consumption of food or on an empty stomach.

The individual may or may not be monitored by a medical practitioner during the course of an asprosin or a functional derivative or a functional fragment regimen. The individual may cease to take asprosin or a functional derivative or a functional fragment once a desirable weight is achieved and may resume taking asprosin or a functional derivative or a functional fragment if the individual becomes in need of gaining weight at a later point in time. In the event that an individual exceeds a suitable amount of asprosin or a functional derivative or a functional fragment such that too much weight is gained, the individual may reduce their weight by any suitable means, including by exercise, reducing caloric intake, and/or taking an inhibitor of asprosin, for example.

V. Individuals in Need of Weight Loss and/or in Need of Improved Glucose Control Embodiments of the disclosure include methods and compositions for decreasing weight in an individual in need of weight loss. The individual may be in need of a decrease in adipose mass, for example. The individual may be in need of weight loss for a variety of reasons, including because of a medical condition or state or for another reason. In cases wherein the individual is in need of weight loss because of a medical condition, the medical condition may or may not be a genetic condition and may or may not be an inherited condition. The cause of being in need of weight loss may be from genetics, metabolism, and/or illness. In specific embodiments, the medical condition has being overweight or obese as a symptom. In some cases, the symptom of being overweight or obese is present in all individuals with the medical condition, although it may be present in less than all individuals with the medical condition. The symptom of being overweight or obese may be because of a defect in pathways related to adipose metabolic regulation, fat storage, and inflammatory processes, although in some cases being overweight or obese is not directly related to adipose metabolic regulation, fat storage, and inflammatory processes. The individual may be overweight or obese because of diabetes; hypothyroidism; metabolic disorders, including metabolic syndrome; medication side effects; alcoholism; eating disorder; insufficient sleep; limited physical exercise; sedentary lifestyle; poor nutrition; addiction cessation; and/or stress; although in some embodiments such conditions are the result of being overweight or obese.

In particular embodiments, an individual has a defect in glucose control and is determined to need an improvement in such defect. In specific embodiments, the defect in glucose control is that there is an excessive amount of glucose in the blood of the individual. In particular embodiments, an individual has diabetes or is pre-diabetic and may or may not also be overweight or obese. The individual is provided an effective amount of one or more of any inhibitors of asprosin to improve blood glucose control, in specific embodiments, including to reduce the level of excessive blood glucose. Such treatment is provided to the diabetic or pre-diabetic individual and an improvement in blood glucose control occurs. The decrease in blood glucose level may or may not be too normal blood glucose levels. In particular embodiments, in addition to an improvement in blood glucose control, one or more symptoms of diabetes or pre-diabetes is improved upon administration of one or more inhibitors of asprosin. For pre-diabetic individuals, the onset of diabetes is prevented upon use of one or more inhibitors of asprosin. For insulin-resistant individuals, asprosin inhibition results in restoration or improvement of insulin sensitivity, resulting in better glucose clearance, in specific embodiments.

In specific embodiments, an individual in need of weight loss is overweight (BMI between 25 and 29) or obese (BMI of 30 or more). The individual that is subjected to methods and compositions of the disclosure may first be identified by a medical practitioner as being in need of weight loss, and the therapeutic composition may be delivered to the individual for the specific purpose of decreasing weight.

In embodiments of the disclosure, the administration of asprosin or a functional derivative or a functional fragment to an individual does not result in the onset of diabetes in the individual. In specific embodiments, the individual has diabetes or does not have diabetes.

VI. Treatment of Individuals in Need of Weight Loss

In embodiments of the disclosure an individual is determined to be in need of weight loss, such as by measuring their weight and/or by measuring their BMI and/or having an MRI and/or DEXA scan for assessment of adipose mass. The individual may be known to be in need of weight loss or suspected of being in need of weight loss or at risk for being in need of weight loss. An individual may determine themselves that they are in need of weight loss and/or it may be determined by a suitable medical practitioner.

Once the individual is known to be in need of weight loss or known to be at risk or susceptible to being in need of weight loss, they may be given a suitable and effective amount of an inhibitor of asprosin. In specific embodiments, one or more asprosin inhibitors are provided to the individual, such as in a composition or in multiple compositions. A composition comprising asprosin inhibitor may be specifically formulated for a therapeutic application.

An individual may be provided suitable dose(s) of asprosin inhibitor on an as needed basis or as part of a routine regimen. The individual may also be taking other measures and/or compositions to lose weight in addition to taking asprosin inhibitor. The individual may take asprosin inhibitor on a daily basis, weekly basis, monthly basis, and so on. The individual may take asprosin inhibitor with consumption of food or on an empty stomach.

The individual may or may not be monitored by a medical practitioner during the course of an asprosin inhibitor regimen. The individual may cease to take asprosin inhibitor once a desirable weight is achieved and may resume taking asprosin inhibitor if the individual becomes in need of losing weight at a later point in time. In the event that an individual exceeds a suitable amount of asprosin inhibitor such that too much weight is lost, the individual may increase their weight by any suitable means, including by increasing caloric intake and/or taking asprosin or a functional fragment or functional derivative, for example.

VII. Diagnosis of Individuals in Need of Weight Modulation

In certain embodiments, an individual is diagnosed as being in need of an increase in weight or is diagnosed as being susceptible to needing an increase in weight based on the level of asprosin in their body (including in their plasma, for example). A suitable sample may be obtained from the individual and processed either by the party that obtains the sample or by a third party. The sample may be stored and/or transported under suitable conditions prior to analysis. In certain embodiments, when the level of asprosin is determined to be below a certain level, the individual is known to be in need of weight gain or is known to be susceptible to being in need of weight gain, and a suitable amount of asprosin or a functional fragment or functional derivative thereof is provided to the individual. In specific embodiments, a diagnosis is made based on asprosin level not to identify that the individual is in need of weight gain or susceptible to being in need of weight gain but instead for the cause of there being in need of weight gain or susceptibility thereof.

In certain embodiments, an individual is diagnosed as being in need of a decrease in weight or is diagnosed as being susceptible to needing a decrease in weight based on the level of asprosin in their body (including in their plasma, for example). A suitable sample may be obtained from the individual and processed either by the party that obtains the sample or by a third party. The sample may be stored and/or transported under suitable conditions prior to analysis. In certain embodiments, when the level of asprosin is determined to be above a certain level, the individual is known to be in need of weight loss or is known to be susceptible to being in need of weight loss, and a suitable amount of one or more asprosin inhibitors is provided to the individual. In specific embodiments, a diagnosis is made based on asprosin level not to identify that the individual is in need of weight loss or susceptible to being in need of weight loss but instead for the cause of there being in need of weight loss or susceptibility thereof. In specific cases, obese individuals may have duplications of fibrillin-1 (or a region thereof) that causes production of excessive asprosin.

Any suitable means to identify levels of asprosin in the body may be employed. In specific embodiments, sandwich ELISA, western blot, competitive radiolabel binding assay, receptor activity assay, and/or measurement of asprosin-induced intra/extracellular signaling cascades are employed to identify plasma levels of asprosin.

VIII. Pharmaceutical Preparations

Pharmaceutical compositions of the present invention comprise an effective amount of one or more of asprosin (or functional fragment or functional derivative) or of one or more asprosin inhibitors dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one asprosin (or functional fragment or functional derivative) or at least one asprosin inhibitor will be known to those of skill in the art in light of the present disclosure, as exemplified by Remington: The Science and Practice of Pharmacy, 21st Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The asprosin (or functional fragment or functional derivative) or asprosin inhibitor may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The asprosin (or functional fragment or functional derivative) or asprosin inhibitor may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include asprosin (or functional fragment or functional derivative) or asprosin inhibitor, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the asprosin (or functional fragment or functional derivative) or asprosin inhibitor may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, the asprosin (or functional fragment or functional derivative) or asprosin inhibitor are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, asprosin (or functional fragment or functional derivative) or asprosin inhibitor may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641, 515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound asprosin (or functional fragment or functional derivative) or asprosin inhibitor may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

IX. Kits of the Disclosure

Any of the compositions described herein may be comprised in a kit. In a non-limiting example, asprosin (or functional fragment or functional derivative) and/or asprosin inhibitor may be comprised in a kit. The kits will thus comprise, in suitable container means, an asprosin (or functional fragment or functional derivative) and/or asprosin inhibitor.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the asprosin (or functional fragment or functional derivative) and/or asprosin inhibitor and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The asprosin (or functional fragment or functional derivative) or asprosin inhibitor compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The kits of the present invention will also typically include a means for containing the vials in close confinement for commercial sale, such as, e.g., injection and/or blow-molded plastic containers into which the desired vials are retained.

The kit may comprise asprosin (or functional fragment or functional derivative) or asprosin inhibitor formulated as an appetite stimulant or appetite suppressant, respectively.

In specific embodiments, the kit further comprises one or more compositions for weight loss or weight gain, including appetite suppressants or appetite stimulants, for example. In certain embodiments, the kit comprises one or more apparatuses and/or reagents for obtaining a sample from an individual and/or processing thereof.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

An Adipose-Derived Polypeptide Hormone Critical for Maintaining Optimal Fat Mass Neonatal Progeroid Syndrome (NPS) Associated Lipodystrophy—NPS is characterized by congenital, extreme thinness due to a reduction in subcutaneous adipose tissue, predominantly affecting the face and extremities (Hou, et al., 2009; O'Neill, et al., 2007). The phenotype is typically apparent at birth (and even before birth as intrauterine growth retardation) with thin skin and prominent vasculature due to paucity of subcutaneous fat (O'Neill, et al., 2007). Patients display a body mass index (BMI) several standard deviations below normal for age, at all ages (O'Neill, et al., 2007). Although NPS patients appear progeroid, due to facial dysmorphic features and reduced subcutaneous fat, they do not have the usual features of true progeria such as cataracts, premature greying of hair or insulin resistance (O'Neill, et al., 2007). Through clinical examination two individuals were identified with NPS and the mechanism that drives their extreme thinness phenotype is characterized herein. Both patients have extremely low BMIs (FIG. 1b), and grossly display reduced subcutaneous fat predominantly affecting the face and limbs with relative sparing in the gluteal area (FIG. 1a). Both patients have normal fasting plasma glucose and insulin levels suggesting that they have normal insulin sensitivity and glucose handling (O'Neill, et al., 2007). They are the only affected members of their families, initially suggesting either potential de novo mutation or recessive inheritance (FIG. 1b).

Whole Exome Sequencing Identifies 3' FBN1 Mutations in NPS—A combination of whole exome and sanger sequencing identified de novo, heterozygous, 3' mutations in the FBN1 gene in both patients (FIG. 1b, 1c). A literature search for similar cases uncovered five case reports describing both an identical phenotype and FBN1 3' truncating mutations (Graul-Neumann, et al., 2010; Horn & Robinson, et al., 2011; Goldblatt, et al., 2011; Takenouschi, et al., 2013; Jacquinet, et al., 2014). All 7 patients (including those of the disclosure) were diagnosed with NPS and all had truncating mutations within a 71 base pair segment of the approximately 8600 base pair coding region (FIG. 1c). All 7 mutations occur 3' 50 nucleotides of the penultimate exon (FIG. 1c), are predicted to result in escape from nonsense mediated decay, and lead to C-terminal truncation of the fibrillin-1 protein due to frame-shift (FIG. 1d). FBN1 is the gene associated with Marfan syndrome, a connective tissue disorder that typically affects the eyes, large blood vessels such as the aorta, and the skeleton (Pyeritz, et al., 2009). Patients are typically tall, thin and have a long arm-span relative to their height (Pyeritz, et al., 2009). Although the patients of the disclosure grossly looked very different from classic Marfan syndrome patients, careful physical examination uncovered the majority of the features of Marfan syndrome in the patients of the disclosure, based upon the revised Ghent nosology for the diagnosis of Marfan syndrome (Loeys, et al., 2010). This was corroborated by the five published case reports associating NPS with 3' mutations in FBN1 (Graul-Neumann, et al., 2010; Horn & Robinson, et al., 2011; Goldblatt, et al., 2011; Takenouschi, et al., 2013; Jacquinet, et al., 2014). Thus, these NPS patients combine the Marfan syndrome phenotype (vascular, ocular and skeletal features) with partial lipodystrophy. Lipodystrophy gives NPS patients a unique appearance and makes the task of diagnosing the associated Marfan syndrome relatively challenging. This may explain why, prior to identification of FBN1 mutations in these patients, for several decades NPS was described as its own unique clinical entity with no connection to Marfan syndrome (OMIM 264090). Fibrillin-1 is a modular protein in that mutations affecting different modules result in different phenotypes (Marfan syndrome, Acromicric dysplasia, Geleophisic dysplasia, Stiff skin syndrome, Weill-Marchesani syndrome) (Pyeritz, et al., 2009; Davis, et al., 2012). Thus, the association of yet another syndrome with fibrillin-1 mutations is not surprising. With a clinical and molecular diagnosis secure, the present example elucidates the mechanism by which fibrillin-1 C-terminal truncating mutations result in lipodystrophy.

Figure 2B:
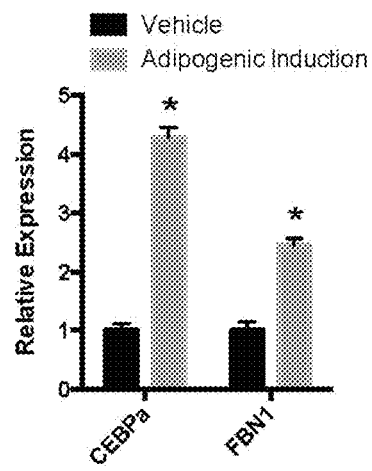
Figure 2C:
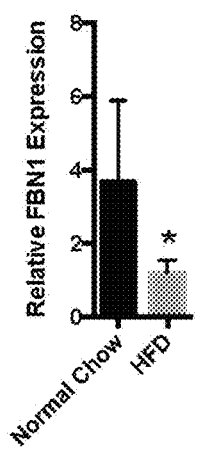

FBN1 is highly and dynamically expressed in white adipose tissue—FBN1 is expressed at high levels in human adipose tissue (Biogps.org, Homo sapien probe set: 202765_s_at), in accord with the NPS phenotype of reduced subcutaneous fat. In mice, Fbn1 is specifically expressed in white adipose tissue compared with brown adipose tissue and skeletal muscle (FIG. 2a). Differentiation of human preadipocytes into adipocytes resulted in an increase in FBN1 expression (FIG. 2b), whereas a reduction in Fbn1 expression in inguinal adipose tissue was observed in mice exposed for several weeks to a high fat diet (FIG. 2c).

Asprosin is a circulating, C-terminal cleavage product of profibrillin—Fibrillin-1 is made as a 2871 amino acid proprotein, which is secreted from cells and cleaved at the C-terminus by an extracellular protease called furin (Milewicz, et al., 1995; Ritty, et al., 1999; Raghunath, et al., 1999; Wallis, et al., 2003). This results in the release of a 140 amino acid C-terminal cleavage product (CT polypeptide), and mature fibrillin-1 that serves as an extracellular matrix component (Milewicz, et al., 1995; Ritty, et al., 1999; Raghunath, et al., 1999; Wallis, et al., 2003). All seven NPS mutations are clustered around the cleavage site, resulting in a heterozygous loss of the CT polypeptide (FIG. 1d). The CT polypeptide shows the highest evolutionary conservation compared with other parts of the protein, and when compared with other species, suggesting an important biological role (FIG. 3a, 3b). It was considered that under normal physiological conditions the CT polypeptide remains stable and has an independent function related to the NPS phenotype. Western blotting confirmed the presence of a unique, discreet 16-kDa cross-reacting entity in plasma from humans and mice (FIG. 3c, 3d). Using plasma from obese mice and humans, it was found that the level of the CT polypeptide was proportional to adiposity in both species (FIG. 3c, 3d). Because FBN1 is highly expressed in white adipose tissue and the NPS phenotype is clinically distinguished by a reduction in white adipose mass, the CT polypeptide was named Asprosin after Aspros, Greek for "white".

Asprosin rescues the NPS associated adipogenic differentiation defect in vitro—The impact of NPS mutations was tested on adipogenic differentiation of cells in vitro using dermal fibroblasts from patients with NPS and unaffected control subjects. Cells were exposed to an adipogenic induction cocktail for seven days that induces increased expression of a number of transcription factors and fat specific genes (Jaager, et al., 2012). Compared with WT cells, NPS mutant fibroblasts were strikingly defective in adipogenic differentiation (FIG. 4a). This defect could be rescued by overexpressing either WT FBN1 (FIG. 4d) or a secreted form of asprosin, but not by asprosin expressed without a signal peptide resulting in its intracellular entrapment (FIG. 4c, 4e, 4f). To confirm the extracellular seat of action of asprosin's adipogenic effect, recombinant asprosin was generated in E. coli. Addition of recombinant asprosin to culture media promoted adipogenic differentiation in WT cells (FIG. 4g), and was sufficient to rescue the adipogenic defect in NPS mutant cells (FIG. 4h).

Figure 7A:
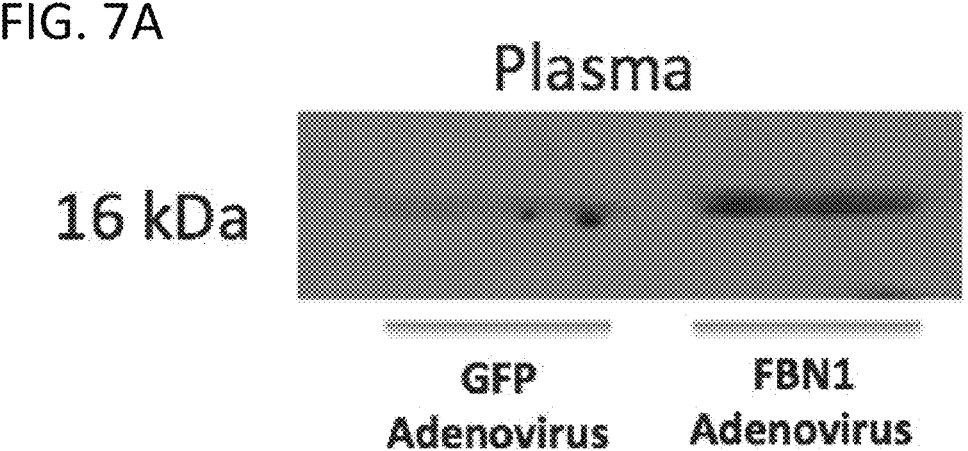
FIG. 7A-7B: FBN1 Adenovirus or Asprosin injection increase the amount of circulating Asprosin—7A, Western blot analysis targeted against Asprosin was performed on plasma from WT mice subjected to a one-time tail vein injection of $10^{11}$ viral particles of adenovirus carrying cDNA (under control of the CMV promoter) for FBN1 or GFP. Measurements were conducted 10 days after the adenoviral injection. 7B, Western blot analysis targeted against Asprosin was performed on plasma from WT mice subjected to dailysubcutaneous injection of 2.6 micro molar recombinant Asprosin or GFP for 10 days. Measurements were conducted 10 days after the initial injection.
Figure 7B:
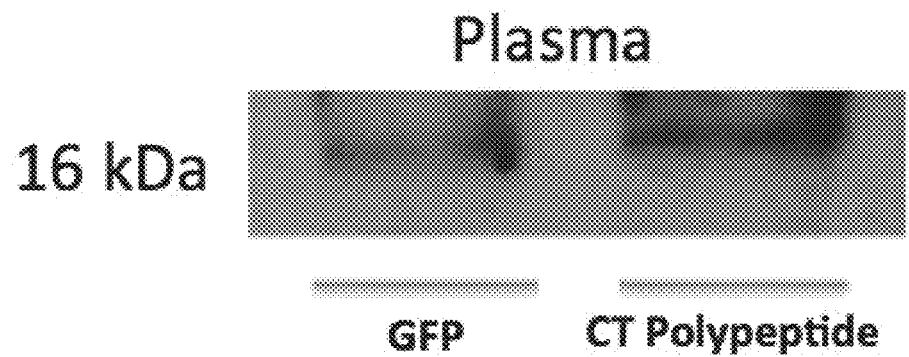
Figure 9A:
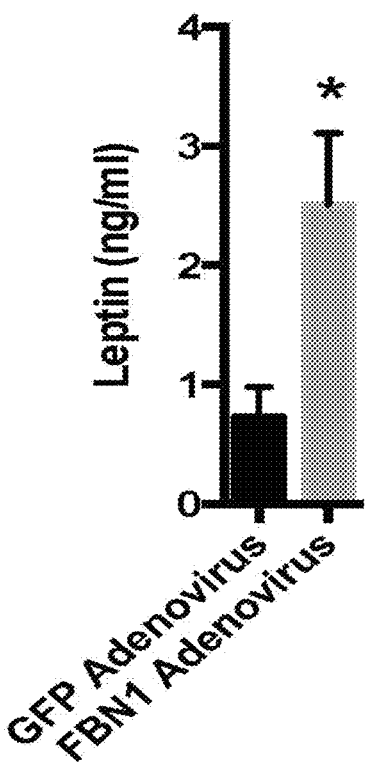
FIG. 9A-9D: Increased circulating Asprosin results in higher plasma levels of adipose derived hormones—9A, 9B Leptin and Adiponectin were measured in plasma from 4-hour fasted WT mice subjected to a one-time tail vein injection of $10^{11}$ viral particles of adenovirus carrying cDNA (under control of the CMV promoter) for FBN1 or GFP (n=6 in each group). Measurements were conducted 10 days after the adenoviral injection. 9C, 9D Leptin and Adiponectin were measured in plasma from 4-hour fasted WT mice subjected to daily subcutaneous injection of 2.6 micro molar recombinant Asprosin or GFP for 10 days (n=6 in each group). Measurements were conducted 10 days after the initial injection.
Figure 9B:
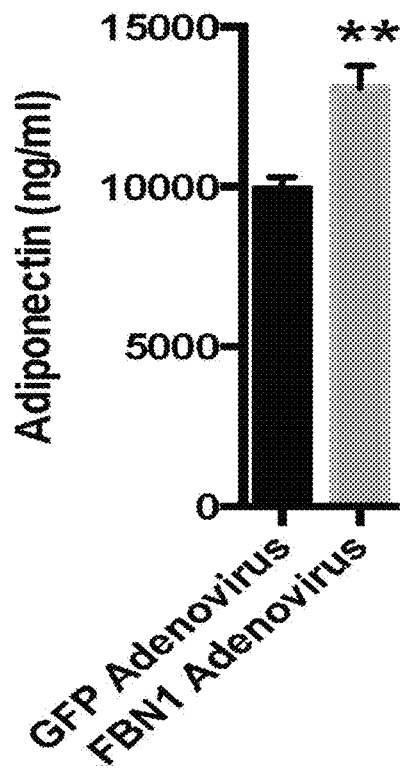
Figure 9C:
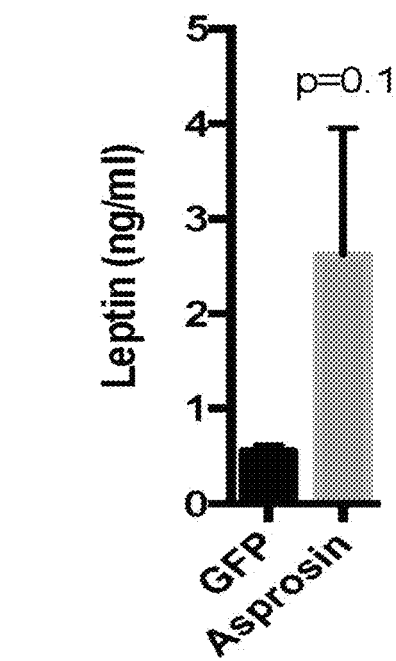
Figure 9D:
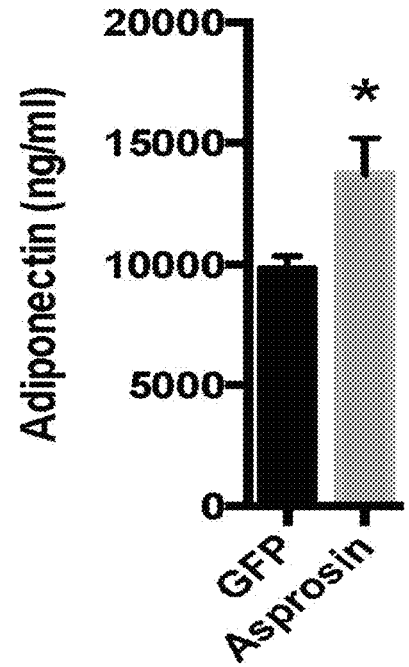
Figure 10A:
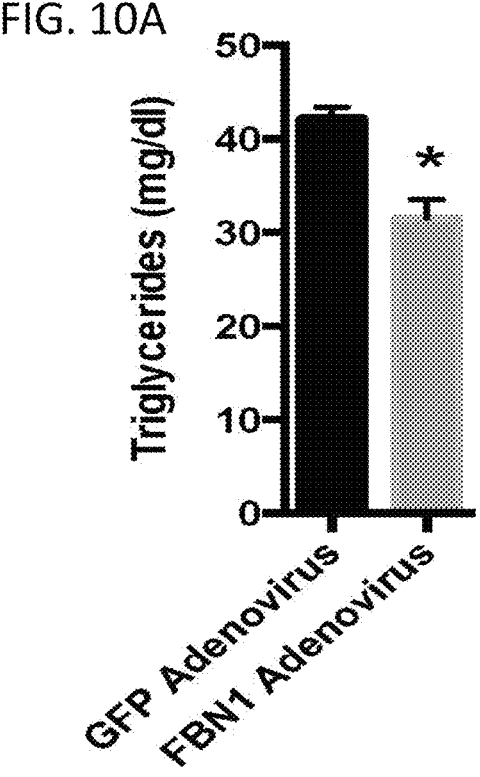
FIG. 10A-10D: Increased circulating Asprosin results in lower plasma lipids—10A, 10B Triglycerides and Free Fatty Acids were measured in plasma from 4-hour fasted WT mice subjected to a one-time tail vein injection of $10^{11}$ viral particles of adenovirus carrying cDNA (under control of the CMV promoter) for FBN1 or GFP (n=6 in each group). Measurements were conducted 10 days after the adenoviral injection. 10C, 10D Triglycerides and Free Fatty Acids were measured in plasma from 4-hour fasted WT mice subjected to daily subcutaneous injection of 2.6 micro molar recombinant Asprosin or GFP for 10 days (n=6 in each group). Measurements were conducted 10 days after the initial injection.
Figure 10B:
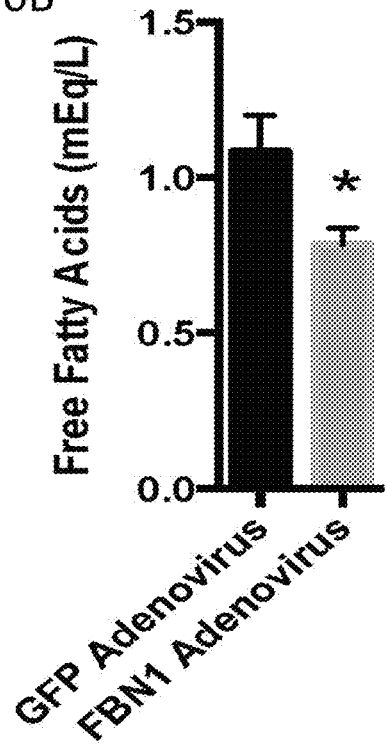
Figure 10C:
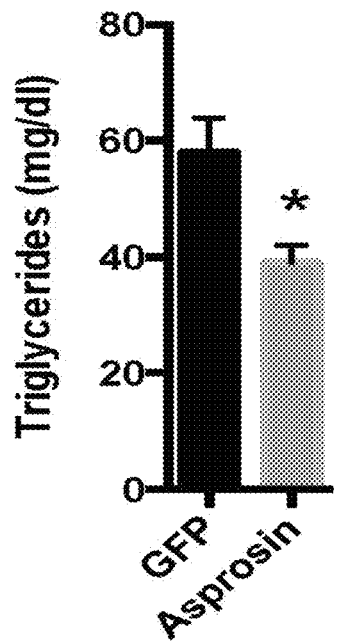
Figure 10D:
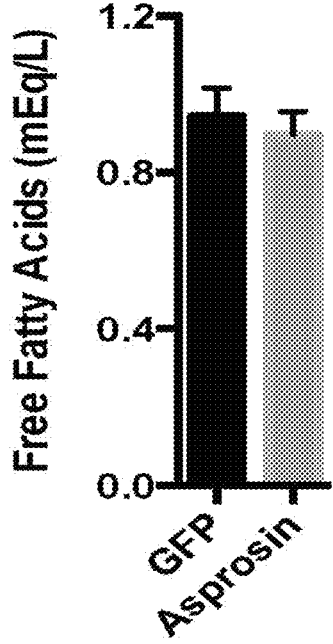
Figure 11A:
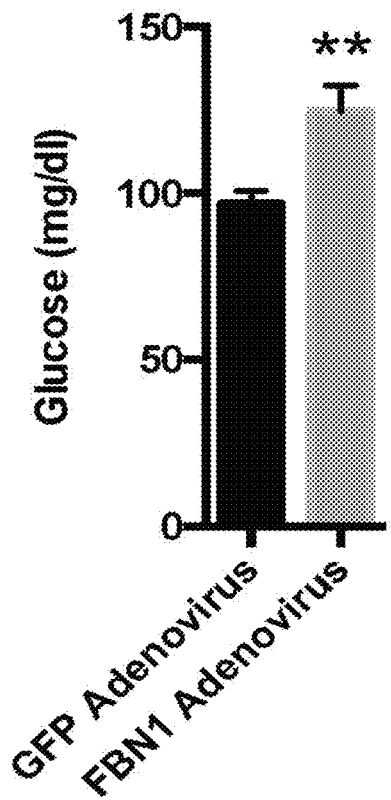
FIG. 11A-11D: Increased circulating Asprosin results in hyperglycemia and hyperinsulinism—11A, 11B Glucose and Insulin were measured in plasma from 4-hour fasted WT mice subjected to a one-time tail vein injection of $10^{11}$ viral particles of adenovirus carrying cDNA (under control of the CMV promoter) for FBN1 or GFP (n=6 in each group).Measurements were conducted 10 days after the adenoviral injection. 11C, 11D Glucose and Insulin were measured in plasma from 4-hour fasted WT mice subjected to daily subcutaneous injection of 2.6 micro molar recombinant Asprosin or GFP for 10 days (n=6 in each group). Measurements were conducted 10 days after the initial injection.
Figure 11B:
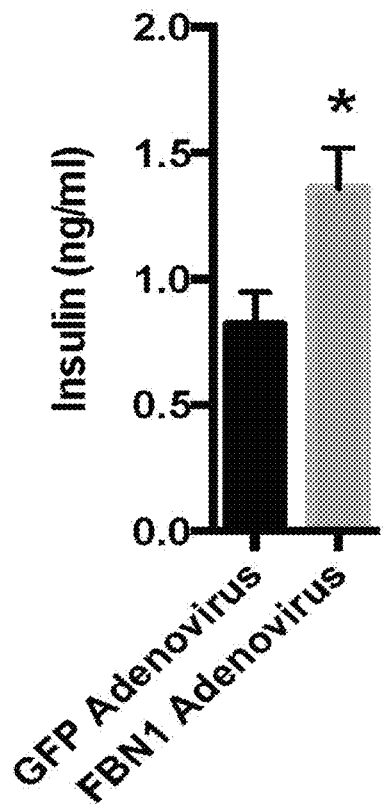
Figure 11C:
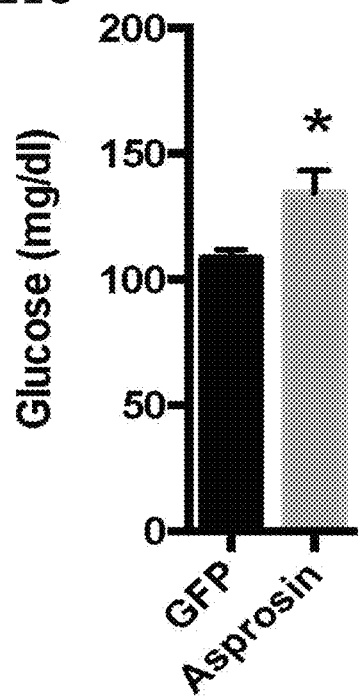
Figure 11D:
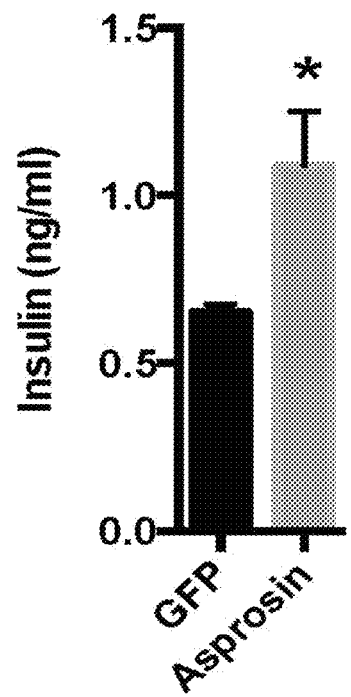

High circulating Asprosin is obesogenic and diabetogenic—To initially test the effect of asprosin in vivo, it was expressed in the liver using adenoviruses carrying cDNA for WT FBN1 or GFP under control of the CMV promoter in standard-chow fed WT mice. Large amounts of asprosin were present in the circulation in mice exposed to the FBN1 adenovirus (FIG. 7), suggesting correct secretion and cleavage of profibrillin by the liver. Ten days following adenoviral injection, MRI scans on the mice showed a 2.5 fold increase in fat mass (FIG. 5a) in mice with greater circulating asprosin, but no change in lean mass (FIG. 5b). The body weight of such mice was proportionally increased over that of control mice (FIG. 5c).

A second approach relied on daily subcutaneous injections of highly purified recombinant asprosin or GFP for ten days in standard-chow fed WT mice. Similar to the adenoviral approach, ten days of daily subcutaneous asprosin injection caused a significant increase in fat mass compared with GFP injection (FIG. 5d). In contrast to the adenovirus experiment, the lean mass of both asprosin and GFP injected mice showed a slight but significant decrease (FIG. 5e) that may reflect the stress imposed upon the mice by daily handling and injection. Regardless, both approaches demonstrated that acutely increasing the amount of circulating asprosin drives fat expansion in vivo. In both experiments, microscopy of inguinal white fat showed a larger fat cell volume in mice exposed to asprosin (FIG. 8). Consistent with greater adiposity in these mice, there were higher levels of plasma leptin and adiponectin, adipose-derived hormones whose circulating levels are known to be directly proportional to fat mass (FIG. 9). Concurrently, there were lower levels of plasma triglycerides and free fatty acids (FIG. 10) that may reflect greater lipid sequestration in the larger adipocytes.

Given that there were the beginnings of obesity in mice exposed to greater circulating asprosin, glucose homeostasis was assayed in these animals. Fasted, asprosin-treated mice showed hyperglycemia and hyperinsulinemia (FIG. 11), suggesting insulin resistance. Both, glucose and insulin tolerance tests were consistent with a diabetogenic effect of high circulating asprosin (FIG. 5g, 5h, 5i, 5j). In accord with a state of obesity and insulin resistance, there was increased lipid accumulation in the livers of animals exposed to greater circulating asprosin (FIG. 12). In summary, an acute increase in circulating asprosin was found to have a potent obesogenic and diabetogenic effect in mice.

Figure 6A:
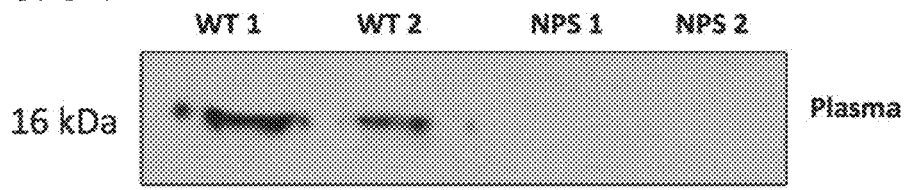
FIG. 6A-6D: Dominant negative effect of truncated profibrillin—6A, Western blot analysis targeted against Asprosin was performed on plasma from NPS patients and unaffected control subjects (WT). 6B, Western blot analysis targeted against Asprosin was performed on cell culture media from human dermal fibroblasts from NPS patients (NPS) or unaffected control subjects (WT) exposed to adipogenic induction for 7 days, and concurrently exposed to vehicle or Monensin to block the secretory pathway. 6C, Animated depiction of expression constructs expressing WT fibrillin-1 (WT FBN1) or mutant profibrillin carrying the c.8207_8208Ins1bp mutation that induces a frame-shift and C-terminal truncation (FBN1 NTΔ). 6D, Western blot analysis targeted against Asprosin was performed on cell culture media from human dermal fibroblasts from unaffected control subjects (WT) exposed to adipogenic induction for 7 days, and concurrently exposed to expression constructs driving GFP or mutant, truncated profibrillin (FBN1 NTΔ), along with vehicle or Monensin to block the secretory pathway.
Figure 6B:
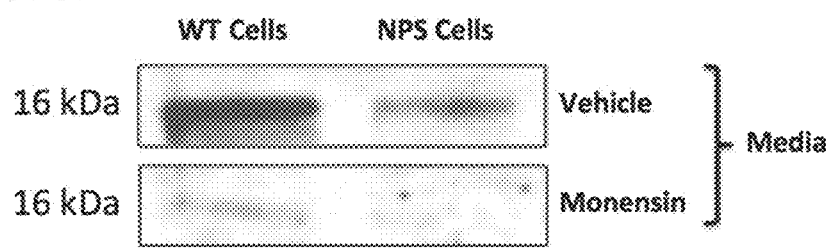
Figure 6C:
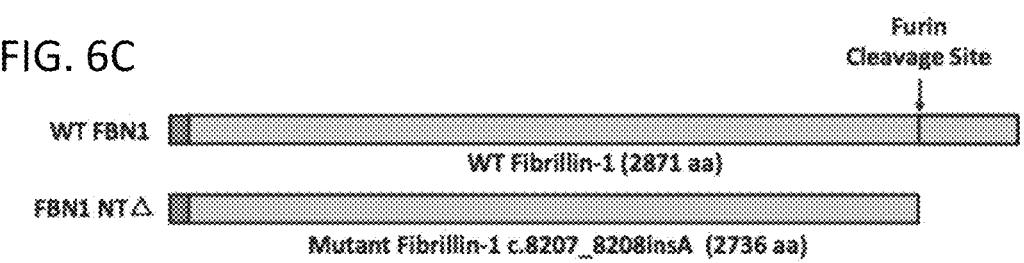
Figure 6D:
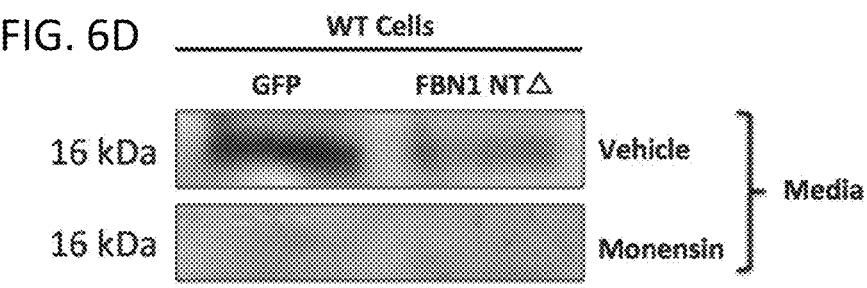
Figure 13:
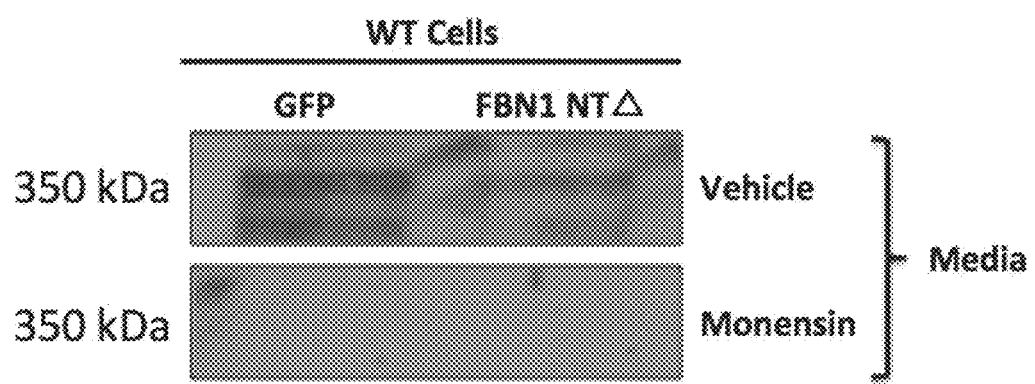
FIG. 13: Dominant negative effect of truncated profibrillin on fibrillin-1 secretion—Western blot analysis targeted against fibrillin-1 was performed on cell culture media from human dermal fibroblasts from unaffected control subjects (WT) exposed to adipogenic induction for 7 days, and concurrently exposed to expression constructs driving GFP or mutant, truncated profibrillin (FBN1 NTΔ), along with vehicle or Monensin to block the secretory pathway.

Dominant negative effect of truncated profibrillin—In addition to being extremely lean, NPS patients are also insulin sensitive (O'Neill, et al., 2007). The opposite physiological profile of mice exposed to too much circulating asprosin corroborates that the NPS phenotype is likely due to reduced circulating asprosin levels. Their heterozygous genotype predicts that NPS patients should have half the circulating asprosin compared with unaffected controls, but there was no detectable circulating asprosin at all in these patients (FIG. 6a). It has recently been shown that the CT polypeptide is necessary for profibrillin secretion from cells (Jensen, et al., 2014). In its absence, the truncated profibrillin that escapes nonsense mediated decay remains trapped intracellularly (Jensen, et al., 2014). Thus, it was considered that the mutant, truncated profibrillin in NPS acts in a dominant negative fashion to prevent secretion of profibrillin from the WT allele. This could also explain why the NPS phenotype is different from classic Marfan syndrome, at least in patients with more N-terminal truncations that then undergo nonsense mediated decay, or whole gene deletions—both of which would not express the truncated profibrillin. In order to test this theory, levels of asprosin were assayed in cell culture media from NPS cells, as well as from WT cells with overexpression of mutant, truncated profibrillin. In both instances, there were markedly reduced asprosin levels in the media, as expected (FIG. 6b, 6d). Additionally, overexpression of mutant profibrillin in WT cells was sufficient to reduce the amount of fibrillin-1 secretion into the media, suggesting a dominant negative mode of pathogenesis for the Marfan syndrome phenotype seen with NPS (FIG. 13).

Methods

Study Subjects and Ethics Statement—Informed consent was obtained prior to participation from all subjects under one of three Institutional Review Board approved protocols at Baylor College of Medicine.

Clinical Evaluation—Clinicians assessed study subjects by direct history, physical examination, and family history analysis. Clinical information in the form of chart records and notes was reviewed. Interviews with these subjects were also conducted by telephone. Families were interviewed together with the patients. Whenever available, reports from previous diagnostic studies, operative reports, or radiologic studies were reviewed. After informed consent, skin biopsies for isolation of dermal fibroblasts were performed under appropriate anesthetic and universal precautions.

Whole-Exome Capture and Sequencing—Genomic DNA from patient #1 and her parents was subjected to whole exome sequencing (trio analysis). Methods utilized for whole-exome sequencing have been previously described in detail (Lupski, et al., 2013). In summary, 1 mg of genomic DNA was fragmented by sonication in a Covaris plate (Covaris, Inc. Woburn, Mass.). Genomic DNA samples were constructed into Illumina paired-end libraries as described (Lupski, et al., 2013). Pre-capture libraries were pooled together and hybridized in solution to the BCM-HGSC CORE exome capture design (Bainbridge, et al., 2011) (52 Mb, Nimble-Gen). Captured DNA fragments were sequenced on an Illumina HiSeq 2000 platform producing 9-10 Gb per sample and achieving an average of 90% of the targeted exome bases covered to a minimal depth of 206 or greater.

Data Analysis—Produced sequence reads were mapped and aligned to the GRCh37 (hg19) human genome reference assembly using the HGSC Mercury analysis pipeline. Variants were determined and called using the Atlas2 suite to produce a variant call file (VCF). High-quality variants were annotated using an in-house developed suite of annotation tools.

Sanger Sequencing—Genomic DNA from patient #2 was subjected to sanger sequencing. Primers were designed to encompass exons 65 and 66 including intron-exon boundaries of the FBN1 gene using Primer3. Sanger reads were analyzed using the Lasergene Seqman software.

Animals—10-week old male WT C57/B16 mice were used for all in vivo studies. Mice were housed 2-5 per cage in a 12-hour light/12-hour dark cycle with access to food and water ad libitum. Mice were exposed to adenoviral-mediated transgenesis ($10^{11}$ virus particles per mouse), via tail-vein injections. Mice were injected with 2.6 micro molar recombinant His tagged Asprosin or recombinant GFP daily for 10 days via subcutaneous injection. Mice were sacrificed and plasma and various organs were isolated 10 days after viral infusion or peptide injection. The Baylor College of Medicine Institutional Animal Care and Utilization Committee approved all experiments.

FBN1 and GFP Adenoviruses—Adenovirus carrying FBN1 cDNA was created by cloning the FBN1 coding region under control of the CMV promoter using a standard Ad5 vector system. The corresponding GFP adenovirus was purchased from the Vector Development Core at Baylor College of Medicine.

Recombinant Asprosin and GFP—Human FBN1 (2732-2871 amino acids) cDNA was cloned and subsequently sub-cloned into a pSPE plasmid for expression in E-coli. The fusion protein that was expressed in E. coli is 146 amino acid long comprising of a 6 amino acid His tag on the N-terminus and a 140 amino acid wild type C-terminal FBN1 (2732-2871 amino acids). His-tagged GFP was purchased from Thermo Scientific as the control polypeptide.

Body composition and Serum analyses—Body composition was analyzed with the ECHO-MRI system (Echo medical systems, Texas). Mouse serum was prepared from blood obtained through cardiac puncture and analyzed with the COBAS Integra 400 plus analyzer (Roche). Plasma leptin, FFA, adiponectin and triglyceride levels were measured by using a Mouse Leptin ELISA Kit (Millipore), NEFA C Test Kit (Wako), Mouse Adiponectin ELISA Kit (Millipore) and Serum/plasma triglyceride detection kit (Sigma), respectively.

Histology—Mouse inguinal adipose tissue samples were fixed in 10% formaldehyde for H&E staining. Frozen livers were used for oil-red-0 staining to evaluate hepatic triglyceride content.

Glucose Tolerance Test (GTT) and Insulin Tolerance Test (ITT)—For GTT, intraperitoneal injection of 1.5 g of glucose/kg of body weight was performed after a 6-hour fasting period. For ITT, intraperitoneal injection of regular insulin (Humulin R; 0.75 unit/kg of body weight) was administered after a 4-hour fasting period. Blood glucose levels were measured using a glucometer (Life Scan).

Expression Vectors—WT FBN1 (1-2871 amino acids), 140 amino acid Asprosin (2732-2871 amino acids) and Asprosin with the native 27 amino acid FBN1 signal peptide attached at the N-terminus (amino acid 1-27+amino acid 2732-2871) were sub-cloned under control of the CMV promoter using the pCMV6-Neo vector system. The same vector expressing GFP or empty vector was used as a control.

Cell Culture—Human dermal fibroblasts isolated from NPS subjects or WT dermal fibroblasts from unaffected control subjects were subjected to adipogenic differentiation using standard protocols. To stimulate adipogenesis, medium was supplemented with 2 uM insulin, 1 uM dexamethasone, 0.25 mM isobutyl methyl xanthine and 10-7 M rosiglitazone for 7 days. Standard transfection methods with expression plasmids were used for in vitro transgenesis.

RNA and Protein Analysis—Standard RNA extraction procedures (RNeasy Mini Kit from Qiagen) were employed. Reverse transcription was carried out using the Superscript III kit (Invitrogen) using the manufacturer's protocol. For gene expression analysis, QPCR was performed using sequence-specific primers and probes from Roche (Universal Probe Library). TBP was used as an internal control for all gene-expression assays. Western blotting was performed using standard methods on plasma or cell culture media using a mouse monoclonal antibody directed against Asprosin, which was purchased from Abnova (Catalog# H00002200-M01). The mouse monoclonal antibody against fibrillin-1 was purchased from Abcam (Catalog# ab3090). For western blotting on media, cells were subjected to adipogenic differentiation for 7 days followed by replacing the induction media with serum free DMEM supplemented with Cellgro ITS (insulin, transferrin, selenium) from Mediatech for 3 days. At that time, media was concentrated using the Amicon Ultra-2 Centrifugal filter unit before proceeding with western blotting.

Statistical Methods—All results are presented as mean±SEM. P value was calculated by unpaired Student's t test or ANOVA, as appropriate. *P<0.05, P<0.01, and *P<0.001.

Example 2

Determine the In Vivo Impact of Gain-of-Function of the Fibrillin-1 C-Terminal Polypeptide The Fibrillin-1 protein was identified 50 years ago (Guba, et al., 1964). Much is known about its functions in maintenance of the extracellular matrix (particularly in the aortic smooth muscle) and its role in health and disease (Davis & Summers, et al., 2012; Reinhardt, et al., 1995). Its structure is known as "modular", meaning that mutations in different parts of the protein lead to different clinical outcomes. As such, it has been associated with Marfan Syndrome, Acromicric Dysplasia, Geleophisic Dysplasia, Stiff Skin Syndrome and Weill-Marchesani Syndrome (Davis & Summers, 2012). Using whole exome sequencing, as well as existing literature, it is also associated with a rare, extreme thinness disorder known as Neonatal Progeroid Syndrome (NPS).

NPS is an autosomal-dominant genetic disorder that results in extreme thinness due to a drastic reduction in subcutaneous adipose tissue (FIG. 1) (O'Neill, et al., 2007; Hou, et al., 2009). The phenotype of the patients overlaps with, but is distinct from classic Marfan syndrome, especially when it comes to their lipodystrophy (Graul-Neumann, et al., 2010; Takenouchi, et al., 2013; Horn, et al., 2011; Goldblatt, et al., 2011). Thus, the site and type of mutation was characterized to explain the difference. The 2 patients that were identified in the disclosure and the 4 that have been previously described (Graul-Neumann, et al., 2010; Takenouchi, et al., 2013; Horn, et al., 2011; Goldblatt, et al., 2011) all have Cterminal truncating mutations in the penultimate exon of FBN1. These 6 truncating mutations are within 70 bp of each other in an ~8600 bp gene. Particularly since lipodystrophy has never been described in association with mutations found in other parts of FBN1, it seems clear that a shared feature of these mutant proteins somehow affects fat biology. The studies have revealed an independently functional Fibrillin-1 C-terminal polypeptide, which is normally cleaved off the parent protein (Ritty, et al., 1999; Raghunath, et al., 1999; Wallis, et al., 2003; Milewicz, et al., 1995) after it is secreted from the cell. Preliminary experiments have shown that haploinsufficiency for the C-terminal polypeptide results in defective fat differentiation. A goal is to characterize whether overexpression of this polypeptide is sufficient to make WT and lipodystrophic mice gain fat mass. This would have direct therapeutic implication for both generalized and localized lipodystrophic conditions that result in a loss of fat mass.

One may test the predicted sufficiency of the Fibrillin-1 C-terminal peptide in fat homeostasis in vivo. These studies can assess the impact of the C-terminal peptide on fat accretion ability in mice treated with recombinant C-terminal polypeptide as well as an adenovirus carrying the cDNA for it. Global gene-expression and metabolomic data sets can be generated and mined to develop testable hypotheses regarding the pathways employed by the Fibrillin-1 C-terminal polypeptide.

Experimental Approach:

A. Inject recombinant Fibrillin-1 C-terminal polypeptide and GFP in mice: 8-week-old C57/B16 WT and PPAR gamma null (lipodystrophic) mice are injected with 20 ug each of recombinant C-terminal polypeptide or recombinant GFP using the subcutaneous approach, every two days for a total of five doses. The recombinant polypeptides have been previously generated using bacterial expression followed by purification and endotoxin removal. The dose of 20 ug each was decided on the basis of preliminary data assessing endogenous plasma levels in mice. 8 mice in each sex-matched group are compared in all assays 10 days after injection.

Figure 14:
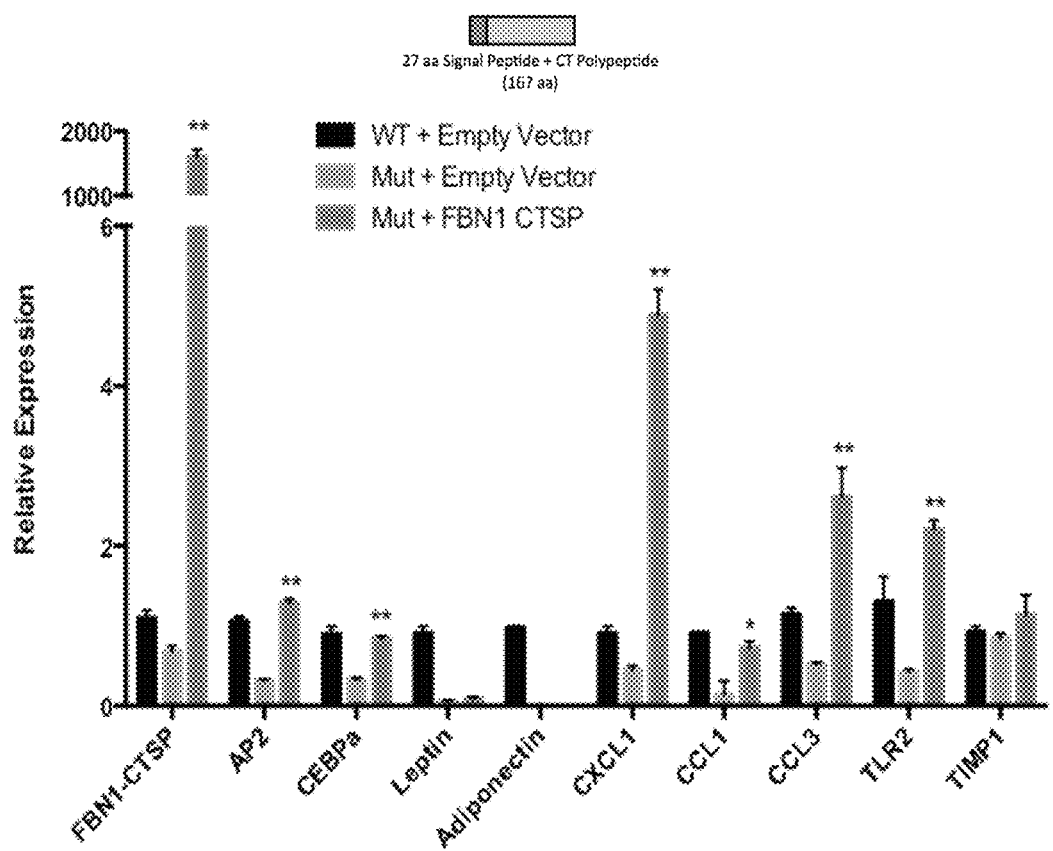
FIG. 14: Dermal fibroblasts from unaffected humans (WT) and patients with NPS (mutant) were differentiated into mature adipocytes using 7-day exposure to an adipogenic medium followed by gene expression analysis. Cells were concurrently exposed to adenovirus carrying no cDNA insert or adenovirus carrying a cDNA insert for Fibrillin-1 C-terminal polypeptide (which may also be referred to herein as asprosin) fused to a signal peptide for 7 days. AP2, CEBPα, Leptin and Adiponectin are adipogenic marker genes. CXCL1, CCL1, CCL3 and TLR2 are inflammogenic marker genes. Only statistical comparison between the 'Mut+Empty Vector' group and the 'Mut+CT Polypeptide' group is indicated on the figure for clarity. Unpaired student's t-test was used for statistical analysis. One asterisk indicates p<0.05, two asterisks p<0.01, and three asterisks p<0.001.

B. Inject adenoviral vectors carrying the Fibrillin-1 C-terminal polypeptide and GFP in mice: 8-week-old C57/B16 WT and PPAR gamma null (lipodystrophic) mice are injected with 1011 viral particles each of previously generated adenovirus expressing C-terminal polypeptide fused to a signal-peptide (FIG. 14) or adenovirus expressing GFP. Based on prior experience using this technique, the majority of the adenoviral load will infect the liver (Chopra, et al., 2008; Chopra, et al., 2011). Following overexpression by hepatocytes, the C-terminal polypeptide, which has been fused with the native Fibrillin-1 signal-peptide, should be secreted by the cells. 8 mice in each sex-matched group are compared for plasma levels of the polypeptide two weeks following the injection, followed by other downstream assays.

C. Measure impact of overexpression of the C-terminal polypeptide on adiposity: Mice are anesthetized and weight and length are recorded. They are placed in the DEXA analyzer (Oosting, et al., 2012) and a scout-scan is performed before performing a true measurement-scan. The exposure dose per mouse is set at 300 µSv. For analysis of the data, regions of interest are defined. The analysis may comprise of a whole body measurement excluding head area. The count data are transformed by software into bone and non-bone components. Information is generated about body weight, body length, bone and fat mass, bone mass density and lean mass of each mouse. The DEXA measurements and analysis are performed at the "Mouse Phenotyping Core Facility" at BCM. After euthanasia, inguinal fat pads are extracted, photographed and weighed.

D. Measure impact of overexpression of the C-terminal polypeptide on global metabolic changes by performing unbiased plasma metabolite profiling: In order to identify organism wide, metabolic changes as a consequence of overexpression of the Fibrillin-1 C-terminal polypeptide, RNAseq is employed. EDTA-Plasma from fasted and fed mice are collected by exsanguination. Frozen, coded samples are sent to Metabolon, Inc. (Durham, N.C.) and accessioned into the Metabolon system by a unique identifier associated with the original source only. Recovery standards are added prior to the first step in the extraction process for quality control purposes. Sample preparation uses a proprietary series of organic and aqueous extractions to remove proteins while allowing maximum recovery of small molecules. Extracted samples are split into equal parts for analysis by gas chromatography/mass spectrometry (GC/MS) and liquid chromatography/mass spectrometry (LC/MS) platforms. Several technical replicate samples are created from a homogeneous pool containing a small amount of each sample. Raw MS data files are loaded into a relational database. Peaks are identified using Metabolon's proprietary peak integration software, and component parts are stored in a separate and specifically designed complex data structure. Compounds are identified by comparison to library entries of purified standards or recurrent unknown entities. Identification of known chemical entities are based on comparison to the over 1,000 commercially available, purified standard compounds registered in LIMS for distribution to both LC and GC platforms. Demographics are presented by frequencies for categorical variables and means±standard deviation (mean±SD) for continuous variables followed by Bonferroni posttest analysis to obtain statistical significance. Approximately 3000 individual plasma metabolites in various classes (acyl-carnitines, organic acids, amino acids, peptides, ions, etc.) can be assayed simultaneously in an unbiased manner using this technique.

E. Assess impact of fat-specific overexpression of the C-terminal polypeptide on fat homeostasis at the level of global gene expression using RNAseq: In order to identify genome wide, transcriptomic changes in adipose tissue as a consequence of overexpression of the Fibrillin-1 C-terminal polypeptide, RNAseq is employed. Total RNA is isolated from previously flash frozen inguinal adipose tissue. Sequencing reactions are done on pooled RNA samples from 5 individual mouse inguinal white fat depots. Four lanes of the flowcell are used for the sequencing of the samples on the Genome Analyzer II. The Genome Analyzer (GA) is run for 38 cycles. The images from the GA are analyzed with the GA pipeline software (v1.3, Illumina software) on cycles 1-38 to undertake image analysis, base calling and sequence alignment to the reference genome. Sequences are aligned with the ELAND software. The aligned reads are used as input for the Illumina CASAVA program (v1.0) to count the sequence reads that align to genes, exons and splice junctions of the reference genome. The raw counts of sequences aligning to features (gene, exons and splice junctions) are normalized by CASAVA by dividing the raw count by the length of the relevant feature. The read counts per gene are used as input for DEGseq and DEseq to identify differentially expressed genes. Both tools are available via the statistics package R and Bioconductor. DEGseq and DESeq use different statistical approaches (Poisson distribution, negative binomial distribution) to estimate probabilities for differential gene expression. A $P \leq 0.001$ and a 2-fold change (normalized) in expression levels are used as cut-off criteria.

One can expect that studies described herein establish sufficiency of the Fibrillin-1 C-terminal polypeptide for the twin processes of fat accretion and inflammation, in specific embodiments. Two gain-of-function approaches are described herein with the aim of assessing the same endpoints. It is expected that even if one approach fails, the other provides conclusive ends. Because of lack of information on the half-life of the native polypeptide in plasma, the recombinant polypeptide experiment could fail if the majority of the peptide is quickly degraded. In that case, it is expected that the adenovirus-mediated transgenesis approach circumvents this issue through constant production of the polypeptide in sufficient amounts to result in gain-of-function. By their very nature, overexpression experiments have the potential to create physiological states that do not reflect the true functionality of the protein being tested. Thus, they need to be interpreted with caution and, if possible, interpreted in the context of concurrent loss-of-function studies. Collective interpretation of gain-of-function and loss-of-function studies proposed herein can enable one to draw the correct conclusions on the true in vivo functions of the Fibrillin-1 C-terminal polypeptide.

Example 3

Figure 15:
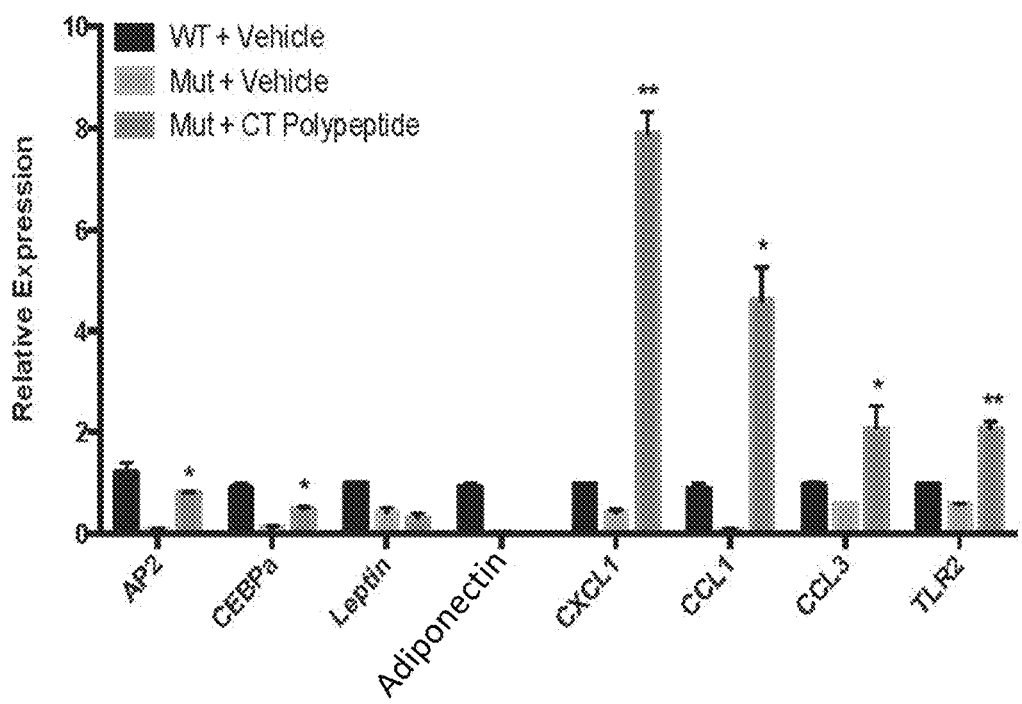
FIG. 15: Dermal fibroblasts from unaffected humans (WT) and patients with NPS (mutant) were differentiated into mature adipocytes using 7-day exposure to an adipogenic medium followed by gene expression analysis. Cells were concurrently exposed to vehicle or 10 ug of the Fibrillin-1 C-terminal polypeptide for 7 days. AP2, CEBPα, Leptin and Adiponectin are adipogenic marker genes. CXCL1, CCL1, CCL3 and TLR2 are inflammogenic marker genes. Only statistical comparison between the 'Mut+Vehicle' group and the 'Mut+CT Polypeptide' group is indicated on the figure for clarity.\ Unpaired student's t-test was used for statistical analysis. One asterisk indicates p<0.05, two asterisks p<0.01, and three asterisks p<0.001.

Determine the In Vivo Impact of Loss-of-Function of the Fibrillin-1 C-Terminal Polypeptide The Fibrillin-1 protein contains a C-terminal cleavage site (RGRKRR motif (SEQ ID NO:5))that has been shown to undergo proteolytic processing by the Furin/PACE family of enzymes (Ritty, et al., 1999; Raghunath, et al., 1999; Wallis, et al., 2003; Milewicz, et al., 1995). This results in two fragments, functional Fibrillin-1 (~2500 amino acids), which is dependent upon the cleavage event for proper insertion into the extracellular matrix (Raghunath, et al., 1999; Milewicz, et al., 1995), and a smaller C-terminal polypeptide (~140 amino acids) whose independent function is unknown. The common result of all 6 heterozygous mutations in FBN1 that result in an NPS phenotype is a loss of the vast majority of the C-terminal polypeptide. If indeed haploinsufficiency of the C-terminal fragment is responsible for the phenotype, then restoring that fragment to its normal levels should result in rescuing the phenotype. This concept was explored in vitro and it was found that restoring the expression of the C-terminal polypeptide as well as simply exposing the mutant cells to the C-terminal polypeptide by adding it to the media, rescued the NPS associated fat differentiation and inflammogenic defects (FIG. 15).

Figure 16:
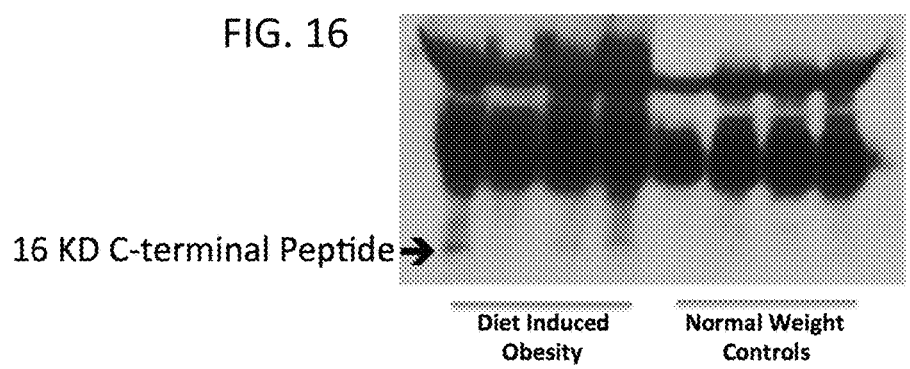
FIG. 16: Western blot analysis was performed on plasma from C57/B16 mice either fed a normal or high fat diet, using a mouse monoclonal antibody that detects the Fibrillin-1 Cterminus specifically. The 16 kd band corresponds to the plasma fraction of the Fibrillin-1 C-terminus.

An analogous approach is utilized in vivo. The circulating C-terminal polypeptide (FIG. 16) is immunologically sequestered using a monoclonal antibody to unravel its necessity for fat accretion and potential for protection against obesity and metabolic syndrome. This would have direct therapeutic implication for both obesity and metabolic syndrome, conditions that result from unmitigated fat accretion.

Experimental Approach:

A. Expose WT and genetically obese mice to a monoclonal antibody targeting the Fibrillin-1 Cterminal Polypeptide: 8-week-old C57/B16 WT and ob/ob (obese mice with a loss-of-function Leptin mutation) mice are injected with 500 ug of anti-CT-Fibrillin-1 IgG or nonspecific IgG using the intraperitoneal approach, daily for a total of five doses. The monoclonal antibody targeting the Fibrillin-1 C-terminal antibody has been previously obtained from Sigma Inc. and validated in house. 8 mice in each sex-matched group are compared in all assays 10 days after injection.

B. Measure impact of loss of the C-terminal polypeptide on adiposity: The impact of neutralization of the Fibrillin-1 C-terminal polypeptide on adiposity is measured using DEXA scans and inguinal fat-pad weights as described in aim 1C. Eight sex-matched, 8-week-old, WT and ob/ob mice exposed to anti-CT-Fibrillin-1 IgG and control IgG are assessed.

C. Measure impact of loss of the C-terminal polypeptide on global metabolic changes by performing unbiased plasma metabolite profiling: EDTA-Plasma from eight sex-matched, 8-week-old, WT and ob/ob mice exposed to anti-CT-Fibrillin-1 IgG and control IgG are collected by exsanguination. Metabolomics analysis is performed as described in aim 1D.

D. Assess impact of loss of the Fibrillin-1 C-terminal polypeptide in fat homeostasis at the level of global gene expression using RNAseq: Total RNA is isolated from previously flash frozen inguinal adipose tissue from fifteen sex-matched, 8-week-old, WT and ob/ob mice exposed to anti-CT-Fibrillin-1 IgG and control IgG. Sequencing reactions are done on pooled RNA samples from 5 individual mouse inguinal white fat depots (N=3). RNAseq analysis is done as described elsewhere herein.

One can expect that studies described herein establish that the Fibrillin-1 C-terminal polypeptide is necessary for fat accretion and protective against obesity, in specific embodiments. The studies considered using the monoclonal antibody targeting the Fibrillin-1 C-terminal polypeptide are not as clean as a genetic ablation study would have been. However, given that a goal is to study the use of such a monoclonal antibody as a therapeutic modality against obesity, it is important to test this compared with a nonspecific antibody, in at least some embodiments. In embodiments wherein this approach establishes a protective role for such an antibody against obesity, those results are confirmed with a genetic knockout study, for example.

Example 4

Figure 17:
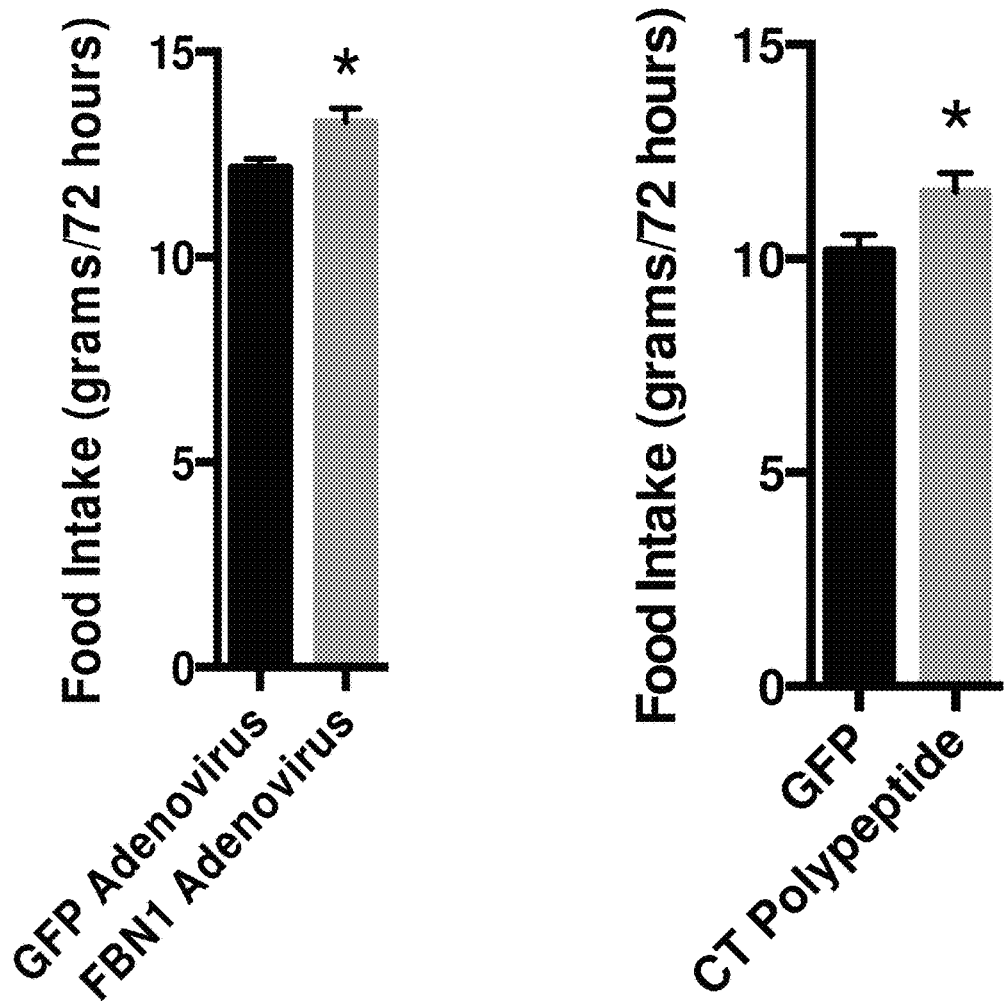
FIG. 17: An increased amount of plasma CT polypeptide (asprosin) results in hyperphagia in mice that have been injected with asprosin.

FIG. 17 shows that an increased amount of plasma CT polypeptide (asprosin) results in hyperphagia in mice that have been injected with asprosin. In embodiments of the disclosure, methods involve providing an effective amount of the CT polypeptide to an individual in need of gaining weight or increasing adipose mass.

In individuals with NPS or another medical condition in which the individual has insufficient adipose mass, the individual may consume a reduced daily caloric load compared to individuals that do not have NPS or another such medical condition. In particular embodiments for these individuals, they may be provided an effective amount of asprosin or a functional derivative thereof in order to increase their daily caloric load, such as by increasing their appetite.

Example 5

Significance of Embodiments of the Disclosure

The discovery of leptin shows that genetic disorders that result in extremes of body weight have the potential to be very informative in the understanding of obesity, diabetes and metabolic syndrome (Friedman, 2009). Described herein is a new polypeptide hormone, asprosin, that is necessary for maintenance of optimal fat mass, and whose origin is tied to an extracellular matrix protein, fibrillin-1. In that, it resembles endostatin, an angiogenic regulator that is a C-terminal cleavage product of a different extracellular matrix protein, Collagen XVIII (O'Reilly, et al., 1997). Thus, it would be reasonable to consider that some extracellular matrix components may have evolved as carriers of C-terminal cleavage products whose functions are distinct from their parent proteins.

Several previous studies have shown how profibrillin is secreted and likely cleaved extracellularly by the furin protease system (Graul-Neumann, et al., 2010; Horn & Robinson, 2011; Goldblatt, et al., 2011; Takenouchi, et al., 2013; Jacquinet, et al., 2014). This cleavage event is necessary for correct processing of fibrillin-1 and its insertion into the extracellular matrix (Graul-Neumann, et al., 2010; Horn & Robinson, 2011; Goldblatt, et al., 2011; Takenouchi, et al., 2013; Jacquinet, et al., 2014). However, the fate of the other cleavage product—the 140 amino acid C-terminal polypeptide has remained unknown. The genotype of NPS patients suggested the possibility that the C-terminal polypeptide, asprosin, has an important role in adipose biology, in embodiments of the disclosure. The data of this disclosure show that asprosin is present in the circulation and is necessary for maintenance of optimal fat mass. Loss of asprosin in humans results in a lipodystrophy, while in mice too much asprosin results in development of fat expansion and glucose intolerance, features of obesity and poor metabolic health. In fact, there are enhanced levels of circulating asprosin in obese states that are correlated with poor metabolic health in mice and humans. In the opposite direction, the phenotype of NPS patients, who have little to no circulating asprosin, display extreme thinness and insulin sensitivity, indicating that in some embodiments decreasing asprosin favors a positive metabolic profile. This is in contrast to some types of lipodystrophy that result in insulin resistance (Nolis, et al., 2013).

In one embodiment, retention of insulin sensitivity in NPS is the sparing of certain fat depots, especially in the gluteal area, that presumably retain their glucose uptake ability in response to insulin. In another embodiment, Asprosin itself promotes insulin resistance in mice, and thus its absence in NPS may have a direct insulin sensitizing effect.

The data indicate that the extreme reduction in circulating Asprosin in NPS, beyond what would be predicted from the NPS genotype, is at least partly the result of a dominant negative effect of the intracellularly trapped mutant profibrillin that escapes nonsense-mediated decay. In specific embodiments, this is why whole gene deletions, non-truncating mutations, or truncating mutations that are proximal to the furin cleavage site, result in Marfan syndrome but not in the additional feature of lipodystrophy that characterizes NPS (Pyeritz, et al., 2009).

Asprosin is remarkable for two reasons. Mice exposed to exogenous Asprosin displayed expansion of their adipose mass and insulin resistance in just 10 days' time. Of note, this was achieved on standard chow rather than a high fat diet. Second, its coding region displays extremely high evolutionary conservation compared with the rest of profibrillin. This indicates a highly conserved function that is likely to be mediated by a cell-surface receptor. The identity of such a postulated receptor is not yet known. Because, based on its expression profile, adipose tissue is likely to be one of the more prevalent sites of asprosin production and secretion, it might seem paradoxical that asprosin is also necessary for fat cell differentiation. However, there are innumerable examples of molecules that serve to regulate their creating organ. Beyond adipogenic differentiation and expansion of fat mass, in some embodiments asprosin also regulates other functions of adipose, and perhaps other tissues. In fact, whether the asprosin-mediated perturbation of glucose homeostasis is an effect of altered fat mass or altered fat activity remains unknown.

The results provide intriguing therapeutic avenues. The most obvious is simply correcting the deficit in NPS patients. However, recombinant asprosin is useful in patients with cachexia secondary to diverse etiologies such as advanced age, cancer, HIV infection, etc., for example. Such patients have significant frailty from reduced adipose mass (Mueller, et al., 2014; Pureza & Florea, 2013; Gelato, et al., 2007; Agarwal, et al., 2013; Kulstad & Schoeller, 2007) among other causes, and might benefit from the adipose expansion afforded by asprosin. Conversely, decreasing circulating asprosin may bring about a reduction in adipose mass and improved glycemic control in patients with obesity and diabetes. In certain embodiments, NPS associated lipodystrophy and obesity are two ends of the asprosin equation, with too little at one end and too much at the other. In any event, correction of circulating asprosin levels in conditions of pathologically altered fat mass affords significant therapeutic benefit, in particular embodiments of the disclosure.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

Agarwal, et al., *Maturitas* 76, 296-302 (2013).
Bainbridge, et al., *Genome Biol.* 12, R68 (2011).
Chopra, et al., *Science* 322:1395-99 (2008).
Chopra, et al., *Cell Metab.* 13:35-43 (2011).
Davis & Summers, *Molecular Genetics and Metabolism* 107, 635-647 (2012).
Esposito, et al., *Plastic Reconstruc Surg.* 118:1048-1057 (2006).
Friedman, American *Journal of Clinical Nutrition* 89, 973S-979S (2009).
Gelato, et al., *Clin Ther.* 29(11):2269-88, 2007.
Goldblatt, et al., *Am. J. Med. Genet. A* 155, 717-720 (2011).
Goldstein & Brown, *Arterioscler. Thromb. Vasc. Biol.* 29, 431-438 (2009).
Graul-Neumann, et al., *Am. J. Med. Genet. A* 152A, 2749-2755 (2010).

Guba & Harsanyi, *Kiserletes orvostudomany* 16:28-34 (1964).
Horn & Robinson, *Am. J. Med. Genet.* A 155, 721-724 (2011).
Hou, *Pediatrics and neonatology* 50, 102-109 (2009).
Jaager, et al., *PLoS ONE* 7, e38833 (2012).
Jacquinet, et al., *Eur J Med Genet* 57, 230-234 (2014).
Jensen, et al., *Proceedings of the National Academy of Sciences* 111, 10155-10160 (2014).
Kulstad, et al., *Curr Opin Clin Nutr Metab Care.* 10(4):488-93, 2007.
Loeys, et al., *J. Med. Genet.* 47, 476-485 (2010).
Lupski, et al., *Genome Med* 5, 57 (2013).
Malik, et al., *Nat Rev Endocrinol* 9, 13-27 (2013).
Milewicz, et al., *J. Clin. Invest.* 95, 2373-2378 (1995).
Morgen & Sørensen, *Nat Rev Endocrinol* 10, 513-514 (2014).
Mueller, et al., *World J Gastroentrol.* 20(28):9361-73, 2014.
Nolis, *J Human Genet.* 59, 16-23 (2013).
O'Neill, et al., *Am. J. Med. Genet.* A 143A, 1421-1430 (2007).
Oosting, et al., *Ped Res.* 72:362-9 (2012).
O'Reilly, et al., *Cell* 88, 277-285 (1997).
Pureza & Florea, *Curr Heart Fail Rep* 10, 307-314 (2013).
Pyeritz, *Heart* 95, 173-175 (2009).
Raghunath, et al., *Journal of cell science* 112 (Pt 7), 1093-1100 (1999).
Rajala, et al., *Endocrin.* 144:3765-73 (2003).
Reinhardt, et al., *Ciba Foundation Symposium.* 192:138-43, discussion 143-127 (1995).
Remington's Pharmaceutical Sciences, 18th Ed. Mack Printing Company, 1990.
Remington: The Science and Practice of Pharmacy, 21st Ed. Lippincott Williams and Wilkins, 2005.
Ritty, et al., *Journal of Biological Chemistry* 274, 8933-8940 (1999).
Rocha, et al., *Nat Rev Cardiol* 6:399-409 (2009).
Shoelson, et al., *Gastroentrol.* 132:2169-80 (2007).
Spiegelman & Flier, Cell 104, 531-543 (2001).
Spiegelman & Flier, Cell 87, 377-389 (1996).
Takenouchi, et al., *Am. J. Med. Genet.* A 161, 3057-3062 (2013).
Trayhurn, et al., *J Nutr.* 136:1935S-39S (2006).
Wallis, et al., *Journal of cellular biochemistry* 90, 641-652 (2003).
Xu, et al., *J Clin Invest.* 112:1821-30 (2003).
Zeyda & Stulnig, et al., *Gerontol* 55:379-86 (2009).

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of increasing the weight of an individual, comprising the step of providing an effective amount of an asprosin polypeptide comprising SEQ ID NO:1 to the individual, wherein the asprosin polypeptide does not comprise fibrillin.

2. The method of claim 1, wherein the polypeptide is comprised in a pharmaceutically acceptable carrier.

3. The method of claim 1, wherein the polypeptide is labeled.

4. A method of stimulating the appetite of an individual, comprising the step of providing an effective amount of recombinant asprosin polypeptide comprising SEQ ID NO:1 to the individual, wherein the recombinant asprosin polypeptide does not comprise fibrillin.

5. The method of claim 4, wherein the polypeptide is comprised in a pharmaceutically acceptable carrier.

6. The method of claim 4, wherein the polypeptide is labeled.

* * * * *

SEQUENCE LISTING

```
<160> NUMBER OF SEQ ID NOS: 5

<210> SEQ ID NO 1
<211> LENGTH: 140
<212> TYPE: PRT
<213> ORGANISM: Homo sapiens

<400> SEQUENCE: 1

Ser Thr Asn Glu Thr Asp Ala Ser Asn Ile Glu Asp Gln Ser Glu Thr
1               5                   10                  15

Glu Ala Asn Val Ser Leu Ala Ser Trp Asp Val Glu Lys Thr Ala Ile
            20                  25                  30

Phe Ala Phe Asn Ile Ser His Val Ser Asn Lys Val Arg Ile Leu Glu
        35                  40                  45

Leu Leu Pro Ala Leu Thr Thr Leu Thr Asn His Asn Arg Tyr Leu Ile
    50                  55                  60

Glu Ser Gly Asn Glu Asp Gly Phe Phe Lys Ile Asn Gln Lys Glu Gly
65                  70                  75                  80

Ile Ser Tyr Leu His Phe Thr Lys Lys Lys Pro Val Ala Gly Thr Tyr
                85                  90                  95

Ser Leu Gln Ile Ser Ser Thr Pro Leu Tyr Lys Lys Lys Glu Leu Asn
            100                 105                 110

Gln Leu Glu Asp Lys Tyr Asp Lys Asp Tyr Leu Ser Gly Glu Leu Gly
        115                 120                 125

Asp Asn Leu Lys Met Lys Ile Gln Val Leu Leu His
    130                 135                 140
```

<210> SEQ ID NO 2
<211> LENGTH: 147
<212> TYPE: PRT
<213> ORGANISM: Escherichia coli

<400> SEQUENCE: 2

Met His His His His His His Ser Thr Asn Glu Thr Asp Ala Ser Asn
1               5                   10                  15

Ile Glu Asp Gln Ser Glu Thr Glu Ala Asn Val Ser Leu Ala Ser Trp
                20                  25                  30

Asp Val Glu Lys Thr Ala Ile Phe Ala Phe Asn Ile Ser His Val Ser
            35                  40                  45

Asn Lys Val Arg Ile Leu Glu Leu Leu Pro Ala Leu Thr Thr Leu Thr
50                  55                  60

Asn His Asn Arg Tyr Leu Ile Glu Ser Gly Asn Glu Asp Gly Phe Phe
65                  70                  75                  80

Lys Ile Asn Gln Lys Glu Gly Ile Ser Tyr Leu His Phe Thr Lys Lys
                85                  90                  95

Lys Pro Val Ala Gly Thr Tyr Ser Leu Gln Ile Ser Ser Thr Pro Leu
            100                 105                 110

Tyr Lys Lys Lys Glu Leu Asn Gln Leu Glu Asp Lys Tyr Asp Lys Asp
        115                 120                 125

Tyr Leu Ser Gly Glu Leu Gly Asp Asn Leu Lys Met Lys Ile Gln Val
    130                 135                 140

Leu Leu His
145

<210> SEQ ID NO 3
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 3

Glu Thr Glu Ala Asn Val Ser Leu Ala Ser Trp Asp Val Glu Lys Thr
1               5                   10                  15

Ala Ile Phe Ala Phe Asn Ile Ser His
            20                  25

<210> SEQ ID NO 4
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 4

Lys Lys Lys Glu Leu Asn Gln Leu Glu Asp Lys Tyr Asp Lys Asp Tyr
1               5                   10                  15

Leu Ser Gly Glu Leu Gly Asp Asn Leu Lys Met Lys
            20                  25

<210> SEQ ID NO 5
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 5

-continued

```
Arg Gly Arg Lys Arg Arg
1               5
```